United States Patent
Oh et al.

(10) Patent No.: US 8,026,390 B2
(45) Date of Patent: Sep. 27, 2011

(54) PHOTOACID GENERATOR CONTAINING AROMATIC RING

(75) Inventors: Jung-Hoon Oh, Cheonan-si (KR);
Dong-Cheol Seo, Cheonan-si (KR);
Jin-Bong Shin, Dobong-gu (KR)

(73) Assignee: Korea Kumho Petrochenicals Co., Ltd., Seoul (KR)

( * ) Notice: Subject to any disclaimer, the term of this patent is extended or adjusted under 35 U.S.C. 154(b) by 254 days.

(21) Appl. No.: 12/384,191

(22) Filed: Apr. 1, 2009

(65) Prior Publication Data
US 2010/0113818 A1 May 6, 2010

(30) Foreign Application Priority Data

Oct. 30, 2008 (KR) ........................ 10-2008-0107039

(51) Int. Cl.
*C07C 309/00* (2006.01)
(52) U.S. Cl. .......................................................... 562/41
(58) Field of Classification Search ........................ None
See application file for complete search history.

(56) References Cited

U.S. PATENT DOCUMENTS

| 2009/0042128 A1* | 2/2009 | Takemoto | 430/281.1 |
| 2010/0099042 A1* | 4/2010 | Ohashi et al. | 430/270.1 |

FOREIGN PATENT DOCUMENTS

| KR | 10-2003-0029837 | 4/2003 |
| KR | 10-2009-0012110 | 2/2009 |

OTHER PUBLICATIONS

Written Opinion issued in connection with corresponding Korean Patent Application No. 2009061235 dated Jul. 15, 2010.

* cited by examiner

*Primary Examiner* — Karl J Puttlitz
(74) *Attorney, Agent, or Firm* — Davidson, Davidson & Kappel, LLC

(57) ABSTRACT

An acid generator represented by the following formula (1) is provided:

[Formula 1]

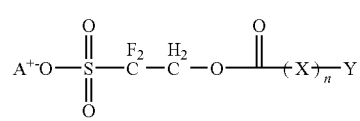

wherein X represents an alkylene group having 1 to 10 carbon atoms, $-X_1-O-X_2-$, or a heteroatom selected from the group consisting of nitrogen, sulfur and fluorine; $X_1$ and $X_2$ each independently represent an alkylene group having 1 to 10 carbon atoms; Y represents a cyclic hydrocarbon group having 5 to 30 carbon atoms and containing one or more aromatic rings, while one or more hydrogen atoms on the ring of the cyclic hydrocarbon group may be substituted by one or more members selected from the group consisting of $-O-Y_1$, $-CO-Y_2$, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group and a cyano group; $Y_1$ and $Y_2$ each independently represent an alkyl group having 1 to 6 carbon atoms; n represents an integer of 0 or 5; and $A^+$ represents an organic counterion.

15 Claims, 16 Drawing Sheets

PHOTOACID GENERATOR CONTAINING AROMATIC RING

This application claims priority to Korean Patent Application No. 10-2008-0107039, filed Oct. 30, 2008, the contents of which are hereby incorporated by reference in their entirety.

BACKGROUND OF THE INVENTION

1. Field of the Invention

The present invention relates to an acid generator containing an aromatic ring, and more particularly, the invention relates to an acid generator containing an aromatic ring, which is included in a chemically amplified resist composition used in semiconductor processes.

2. Description of the Related Art

A chemically amplified resist composition used in the semiconductor fine processing utilizing lithography contains an acid generator, and as the technologies supporting the semiconductor fine processing continue to develop, a demand for resists with higher resolution still exists.

Therefore, in order to produce a resist having an increased resolution and desired properties, a large number of different acid generators have been developed, and in order to improve the diffusion rate of acid and transparency, which are some of the properties associated with high resolution, numerous modifications and experiments in the design of the cation moiety of the salts used as acid generators, have been carried out.

However, in the recent studies of resist compositions, the development of photoacid generators focused on the cation moiety is beginning to face limits in the improvement of resist properties, and there has occurred a problem of reducing effluence into water, which is required as water is used in the immersion ArF processes.

Therefore, based on a number of experimental data and articles reporting that the anion moiety can exert greater influence than the cation moiety on the physical and chemical properties which substantially improve the fluidity of acid and the properties of the resist composition, new inventions associated with the anion moiety of acid generators have recently been achieved. These new inventions are focused on the invention of a photoacid generator which reduces the diffusion rate of acid, and can control the transmissibility of ArF radiation at 193 nm (for example, Korean Patent Application Nos. 10-2006-0104718, 10-2006-0133676, 10-2005-0107599, 10-2006-0114104 and 10-2008-0023406).

SUMMARY OF THE INVENTION

Following the research trend concerning anions as described above, in order to produce an acid generator which can solve the problems of the diffusion rate of acid, the distance of diffusion, absorbance and the like, and has more excellent performance, the present invention provides a novel acid generator which has excellent resolution and line width roughness in a chemically amplified resist composition, and has less effluence into water in ArF immersion processes.

The present invention also provides intermediates used in the production of the acid generator, and a method for synthesizing the intermediate substances.

According to an aspect of the present invention, there is provided an acid generator represented by the following formula (1):

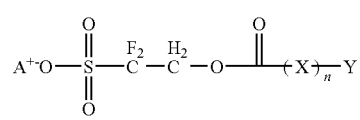

[Formula 1]

wherein X represents an alkylene group having 1 to 10 carbon atoms, $-X_1-O-X_2-$, or a heteroatom selected from the group consisting of nitrogen (N), sulfur (S) and fluorine (F); $X_1$ and $X_2$ each independently represent an alkylene group having 1 to 10 carbon atoms; Y represents a cyclic hydrocarbon group having 5 to 30 carbon atoms and containing one or more aromatic rings, while one or more hydrogen atoms on the ring of the cyclic hydrocarbon group may be substituted by one or more members selected from the group consisting of $-O-Y_1$, $-CO-Y_2$, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group and a cyano group; $Y_1$ and $Y_2$ each independently represent an alkyl group having 1 to 6 carbon atoms; n represents an integer of 0 or 5; and $A^+$ represents an organic counterion.

The moiety $A^+$ is preferably a cation represented by the following formula (2A), formula (2B), formula (3A) or formula (3B):

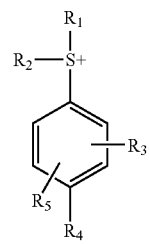

[Formula 2A]

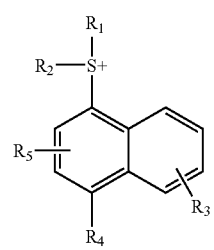

[Formula 2B]

wherein $R_1$ and $R_2$ each independently represent an alkyl group having 1 to 12 carbon atoms, an allyl group having 2 to 12 carbon atoms, a perfluoroalkyl group having 1 to 12 carbon atoms, a benzyl group or an aryl group having 5 to 20 carbon atoms; and $R_3$, $R_4$ and $R_5$ each independently represent a hydrogen atom, an alkyl group having 1 to 12 carbon atoms, a halogen atom, an alkoxy group having 1 to 12 carbon atoms, an aryl group having 5 to 12 carbon atoms, a thiophenoxy group, a thioalkoxy group having 1 to 12 carbon atoms, or an alkoxycarbonylmethoxy group having 1 to 6 carbon atoms;

[Formula 3A]

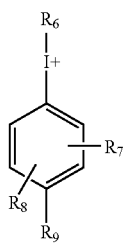

[Formula 3B]

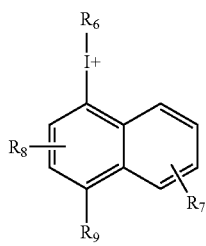

wherein $R_6$ and $R_9$ each independently represent an alkyl group having 1 to 12 carbon atoms, an allyl group having 2 to 12 carbon atoms, a perfluoroalkyl group having 1 to 12 carbon atoms, a benzyl group or an aryl group having 5 to 20 carbon atoms; and $R_7$ and $R_8$ each independently represent a hydrogen atom, an alkyl group having 1 to 12 carbon atoms, a halogen atom, an alkoxy group having 1 to 12 carbon atoms, an aryl group having 5 to 12 carbon atoms, a thiophenoxy group, a thioalkoxy group having 1 to 12 carbon atoms or an alkoxycarbonylmethoxy group having 1 to 6 carbon atoms.

Preferably, the acid generator of formula (1) can be produced by a reaction between a salt represented by the following formula (14) and a compound represented by the following formula (15):

[Formula 14]

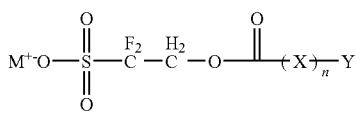

wherein X represents an alkyl group having 1 to 10 carbon atoms, —$X_1$—O—$X_2$— or a heteroatom selected from the group consisting of N, S and F; $X_1$ and $X_2$ each independently represent an alkylene group having 1 to 10 carbon atoms; Y represents a cyclic hydrocarbon group having 5 to 30 carbon atoms and containing one or more aromatic rings, while one or more hydrogen atoms on the ring of the cyclic hydrocarbon group may be substituted by one or more members selected from the group consisting of —O—$Y_1$, —CO—$Y_2$, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group and a cyano group; $Y_1$ and $Y_2$ each independently represent an alkyl group having 1 to 6 carbon atoms; M represents lithium (Li), sodium (Na) or potassium (K); and n represents an integer of 0 or 5;

$A^+Z^-$ [Formula 15]

wherein Z represents $OSO_2CF_3$, $OSO_2C_4F_9$, $OSO_2C_8F_{17}$, $N(CF_3)_2$, $N(C_2F_5)_2$, $N(C_4F_9)_2$, $C(CF_3)_3$, $C(C_2F_5)_3$, $C(C_4F_9)_3$, F, Cl, Br, I, $BF_4$, $ASF_6$ or $PF_6$; and $A^+$ represents an organic counterion.

Preferably, the salt of formula (14) can be produced by reacting an alcohol compound represented by the following formula (16) with a carbonyl chloride compound represented by the following formula (17):

[Formula 16]

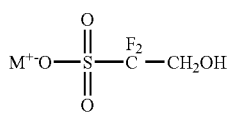

wherein M represents Li, Na or K;

[Formula 17]

$$Cl \overset{O}{\underset{\|}{-C}}(X)_n-Y$$

wherein X represents a monocyclic or polycyclic hydrocarbon group having 3 to 30 carbon atoms, while at least one or more hydrogen atoms on the monocyclic or polycyclic hydrocarbon group may be substituted by an alkyl or alkoxy group having 1 to 10 carbon atoms, the alkyl or alkoxy group being unsubstituted or substituted with an ether group, an ester group, a carbonyl group, an acetal group, an epoxy group, a nitrile group or an aldehyde group, or by a perfluoroalkyl group having 1 to 4 carbon atoms, a hydroxyalkyl group having 1 to 10 carbon atoms or a cyano group; Y represents a phenyl group, a naphthyl group, an anthryl group, a phenanthrenyl group, a fluorenyl group or a pyrene group, while one or more hydrogen atoms on these rings may be substituted by one or more members selected from the group consisting of —O—$Y_1$, —CO—$Y_2$, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group and a cyano group; and $Y_1$ and $Y_2$ each independently represent an alkyl group having 1 to 6 carbon atoms.

Preferably, the alcohol compound of formula (16) can be produced by dissolving an ester compound represented by the following formula (18) in an alcoholic solvent, and then adding a reducing agent dropwise:

[Formula 18]

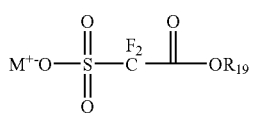

wherein $R_{19}$ represents one selected from the group consisting of hydrogen, methyl, trifluoromethyl, trichloromethyl, tribromomethyl and triiodomethyl; and M represents Li, Na or K.

According to another aspect of the present invention, there is provided a chemically amplified resist composition comprising the acid generator according to the present invention.

The acid generator according to the present invention has an advantage of having a characteristic that the diffusion rate of acid, the distance of diffusion, the acidity, and the transmissibility at the time of using an ArF light source can be appropriately controlled by introducing an anion group containing an aromatic ring.

DESCRIPTION OF THE PREFERRED EMBODIMENTS

Figure 1:
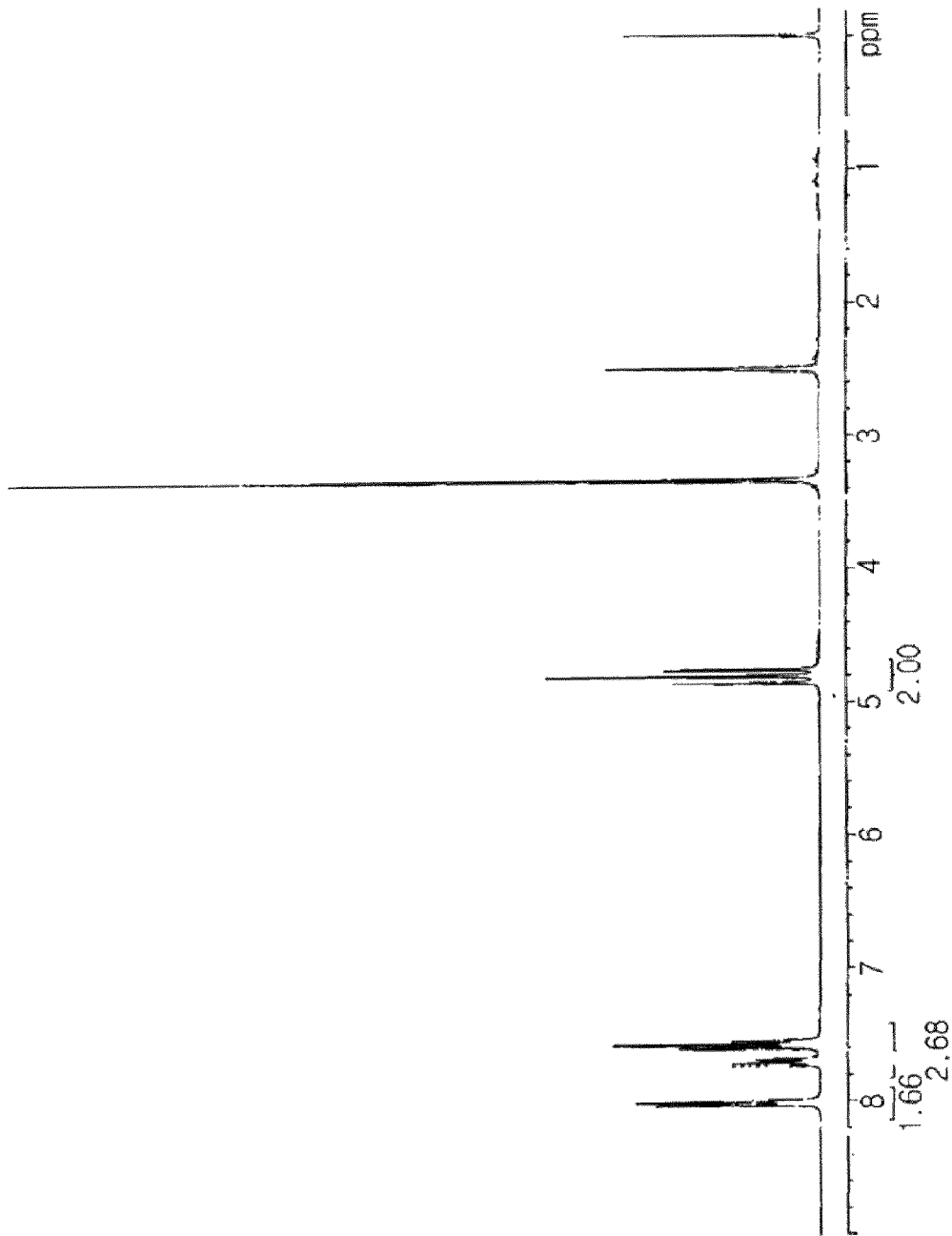
FIG. 1 is a $^1$H-NMR spectrum of a compound produced according to an embodiment of the present invention.

Hereinafter, the present invention will be described in more detail.

According to embodiments of the present invention, there is provided an acid generator which is a compound represented by the following formula (1):

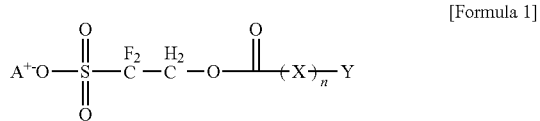

[Formula 1]

wherein X represents an alkylene group having 1 to 10 carbon atoms, $-X_1-O-X_2-$, or a heteroatom selected from the group consisting of N, S and F; $X_1$ and $X_2$ each independently represent an alkylene group having 1 to 10 carbon atoms; Y represents a cyclic hydrocarbon group having 5 to 30 carbon atoms and containing one or more aromatic rings, while one or more hydrogen atoms on the ring of the cyclic hydrocarbon group may be substituted by one or more members selected from the group consisting of $-O-Y_1$, $-CO-Y_2$, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group and a cyano group; $Y_1$ and $Y_2$ each independently represent an alkyl group having 1 to 6 carbon atoms; n represents an integer of 0 or 5; and $A^+$ represents an organic counterion.

Preferred specific examples of X include $-O-$, $-OCH_2-$, $-OCH(Cl)-$, $-CO-$, $-COCH_2-$, $COCH_2CH_2-$, $-CH_2-$, $-CH_2CH_2-$, $-CH_2-O-$, $-CH_2-O-CH_2-$, $-CH_2CH_2-O-$, $-CH_2-O-CH_2CH_2-$, $-CH_2CH_2-CH_2-$, $-CH_2CH_2CH_2-O-$, $-CH_2-O-CH_2CH_2CH_2-$, $-CH_2CH_2-O-CH_2CH_2-$, $-CH_2CH_2CH_2-O-CH_2-$, $-CH(CH_3)-$, $-CH(CH_3)_2CH_2-$, $-CH(CH_2CH_3)-$, $-CH(OCH_3)-$, $-C(CF_3)(OCH_3)-$, $-CH_2-S-$, $-CH_2-S-CH_2-$, $-CH_2CH_2-S-$, $-CH_2-S-CH_2CH_2-$, $-CH_2CH_2-S-CH_2-$, $-CH_2CH_2CH_2-S-$, $-CH_2-S-CH_2CH_2CH_2-$, $-CH_2CH_2-S-CH_2CH_2-$, $-CH_2CH_2CH_2-S-CH_2-$, $-CH(CH_2)CH-$, $-C(CH_2CH_2)-$, $-CH_2CO-$, $-CH_2CH_2CO-$, $-CH(CH_3)CH_2CO-$, $-CH(OH)-$, $-C(OH)(CH_3)-$, $-CH(F)-$, $-CH(Br)-$, $-CH(Br)CH(Br)-$, $-CH=CH-$, $-CH_2CH=CH-$, $-CH=CHCH_2-$, $-CH=CH-O-$, $-CH=CH-S-$, $-CH=CHCO-$, and the like, but the examples of X are not intended to be limited to these.

Examples of the one or more aromatic rings of Y include a benzene ring, a naphthalene ring, an anthracene ring, a phenanthrene ring, a fluorene ring, a pyrene ring, and the like. Preferably, Y may be selected from the group consisting of groups of the following formulas (1-a) to (1-f):

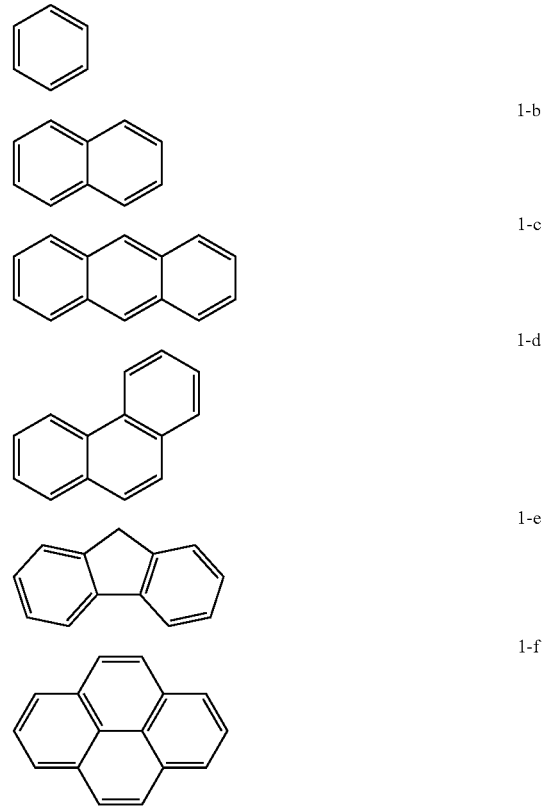

Preferably, the anion moiety of the salt of formula (1) may be any one among the compounds represented by the following formulas (1-i) to (1-xxxxxi):

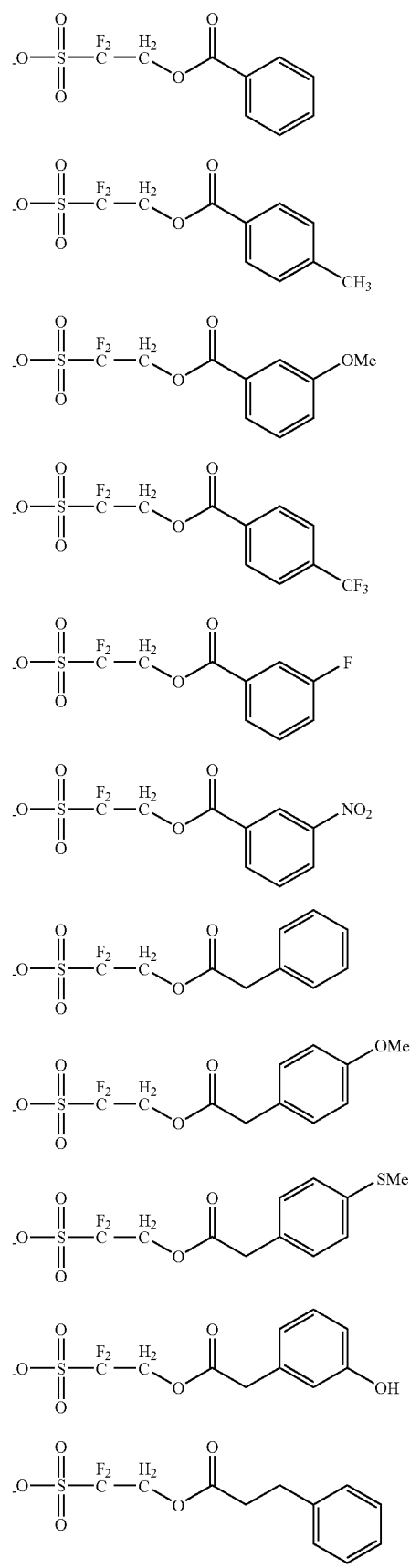
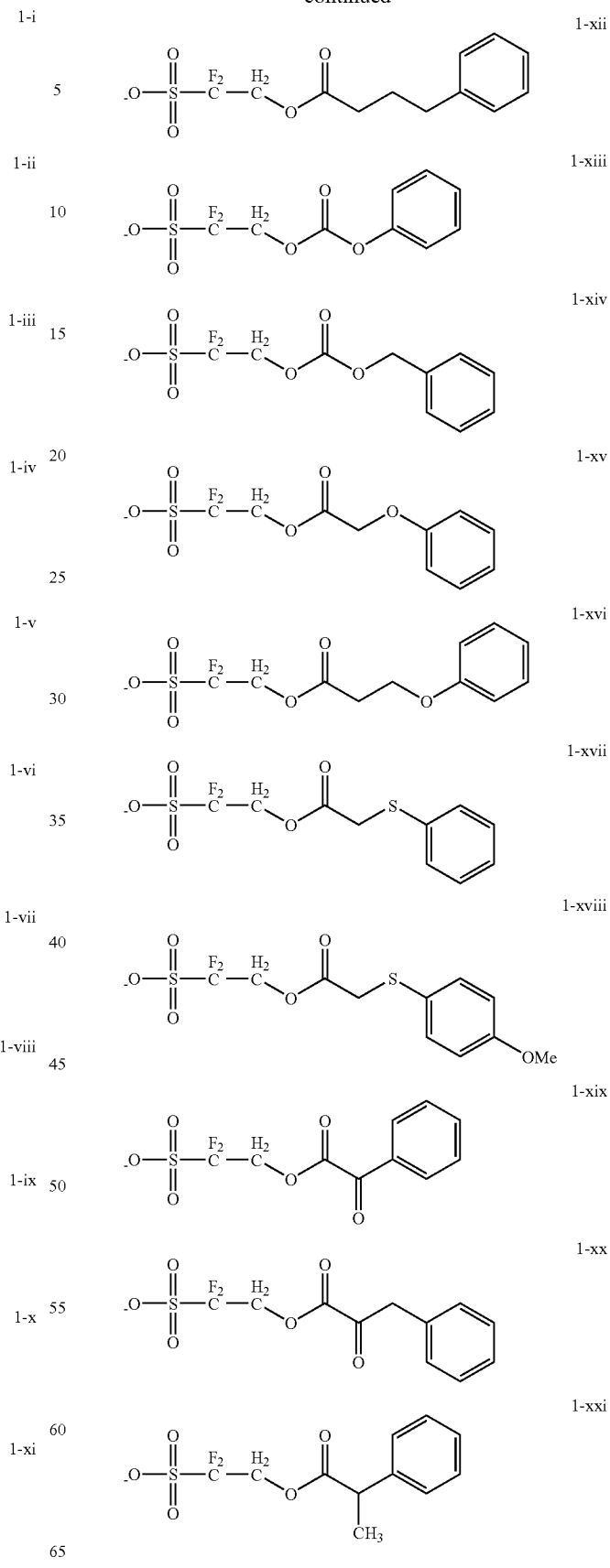

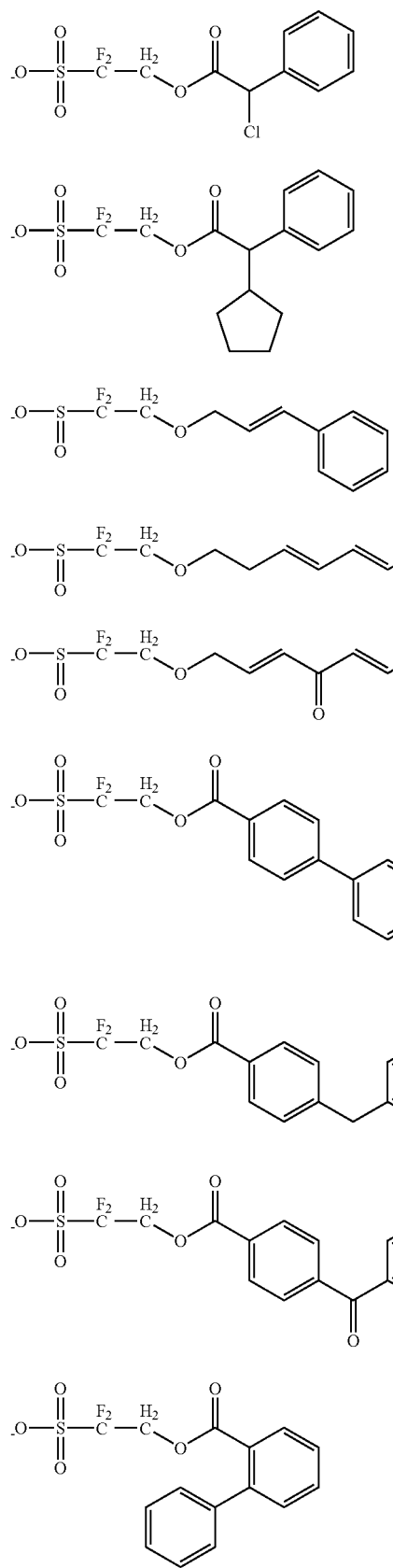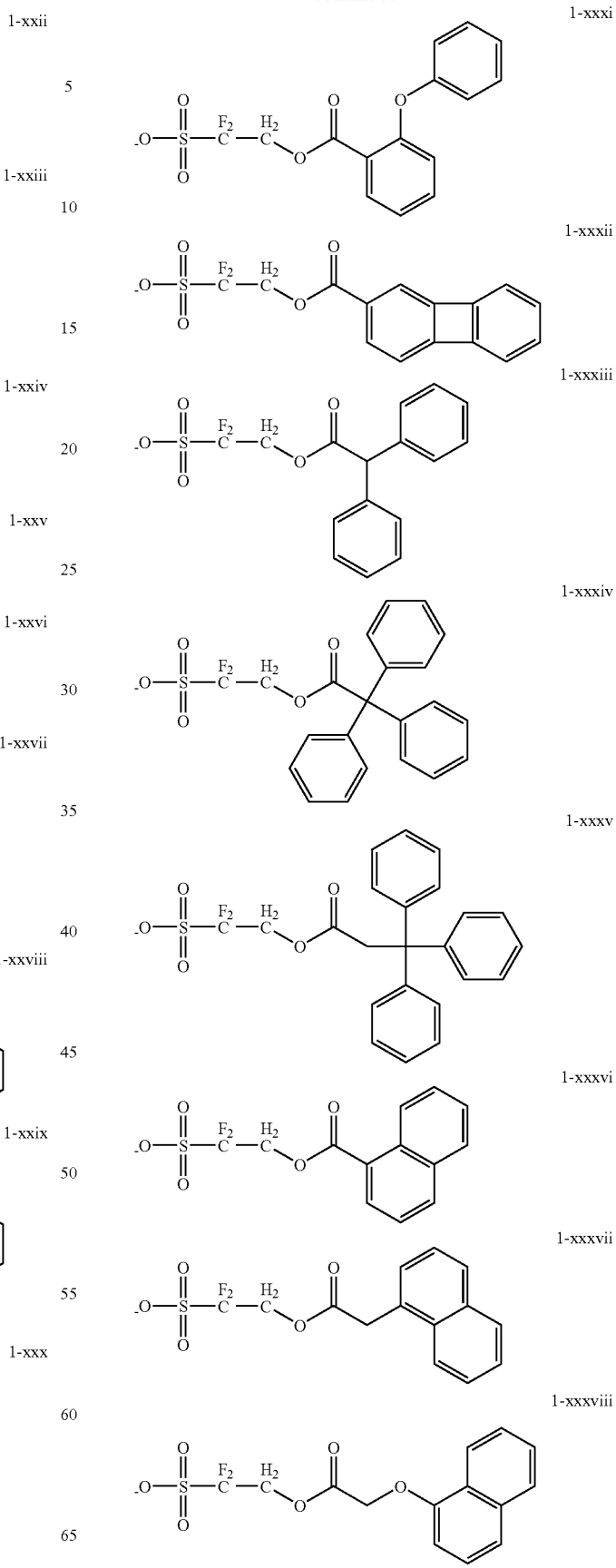

-continued

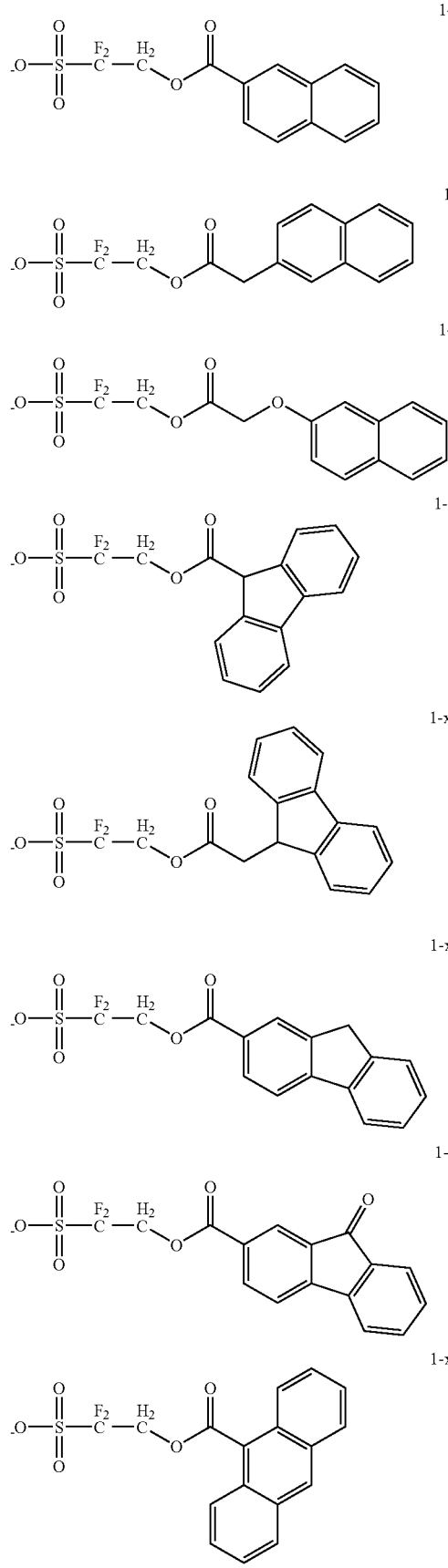

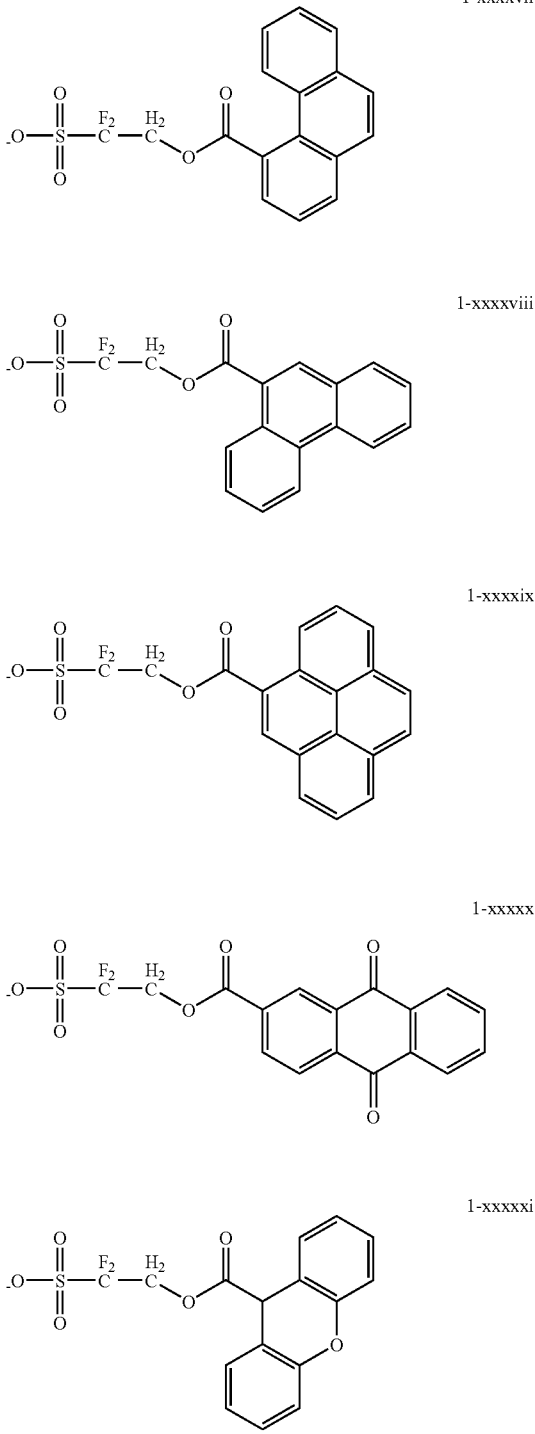

It seems that the acid generator of formula (1) can undergo improvement in the diffusion rate of acid, the distance of diffusion, acidity, transparency and the like, when a hydrocarbon resulting in an anion in a bulky form, a cyclic hydrocarbon having a large number of carbon atoms, or an aromatic ring is introduced into the molecule of the acid generator.

The moiety $A^+$ represents an organic counterion, and according to an embodiment of the present invention, $A^+$ is a cation represented by the following formula (2A) or (2B):

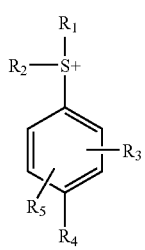

[Formula 2A]

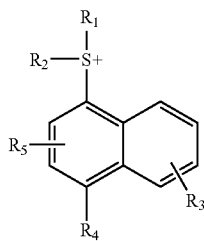

[Formula 2B]

wherein $R_1$ and $R_2$ each independently represent an alkyl group having 1 to 12 carbon atoms, an allyl group having 2 to 12 carbon atoms, a perfluoroalkyl group having 1 to 12 carbon atoms, a benzyl group or an aryl group having 5 to 20 carbon atoms; and $R_3$, $R_4$ and $R_5$ each independently represent a hydrogen atom, an alkyl group having 1 to 12 carbon atoms, a halogen atom, an alkoxy group having 1 to 12 carbon atoms, an aryl group having 5 to 12 carbon atoms, a thiophenoxy group, a thioalkoxy group having 1 to 12 carbon atoms, or an alkoxycarbonylmethoxy group having 1 to 6 carbon atoms.

According to another embodiment, $A^+$ is a cation represented by the following formula (3A) or (3B):

[Formula 3A]

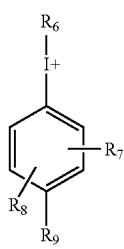

[Formula 3B]

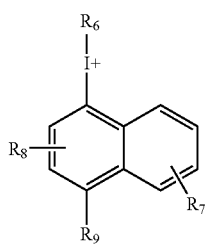

wherein $R_6$ and $R_9$ each independently represent an alkyl group having 1 to 12 carbon atoms, an allyl group having 2 to 12 carbon atoms, a perfluoroalkyl group having 1 to 12 carbon atoms, a benzyl group or an aryl group having 5 to 20 carbon atoms; and $R_7$ and $R_8$ each independently represent a hydrogen atom, an alkyl group having 1 to 12 carbon atoms, a halogen atom, an alkoxy group having 1 to 12 carbon atoms, an aryl group having 5 to 12 carbon atoms, a thiophenoxy group, a thioalkoxy group having 1 to 12 carbon atoms or an alkoxycarbonylmethoxy group having 1 to 6 carbon atoms.

More specifically, the alkyl group among the substituents may be exemplified by methyl, ethyl, propyl, isopropyl, n-butyl, phenyl, hexyl, octyl, or the like, and the alkoxy group may be exemplified by methoxy, ethoxy, propoxy, butoxy, hexyloxy, octyloxy, or the like.

The compounds of the formula (2A) and formula (2B) may be more specifically compounds represented by the following formulas (2-i) to (2-xx):

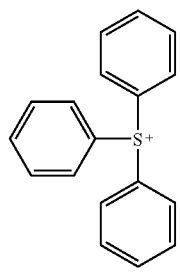

2-i

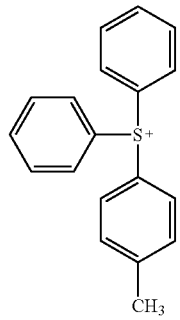

2-ii

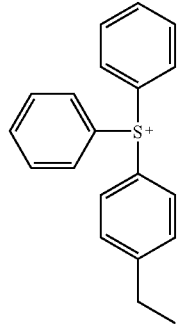

2-iii

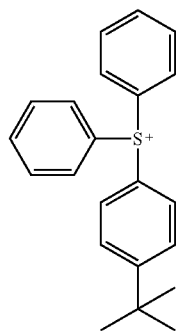

2-iv

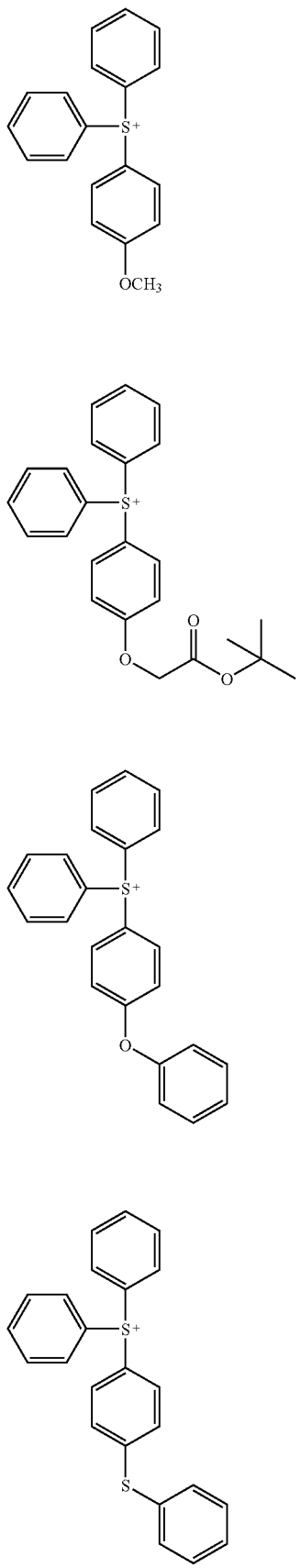
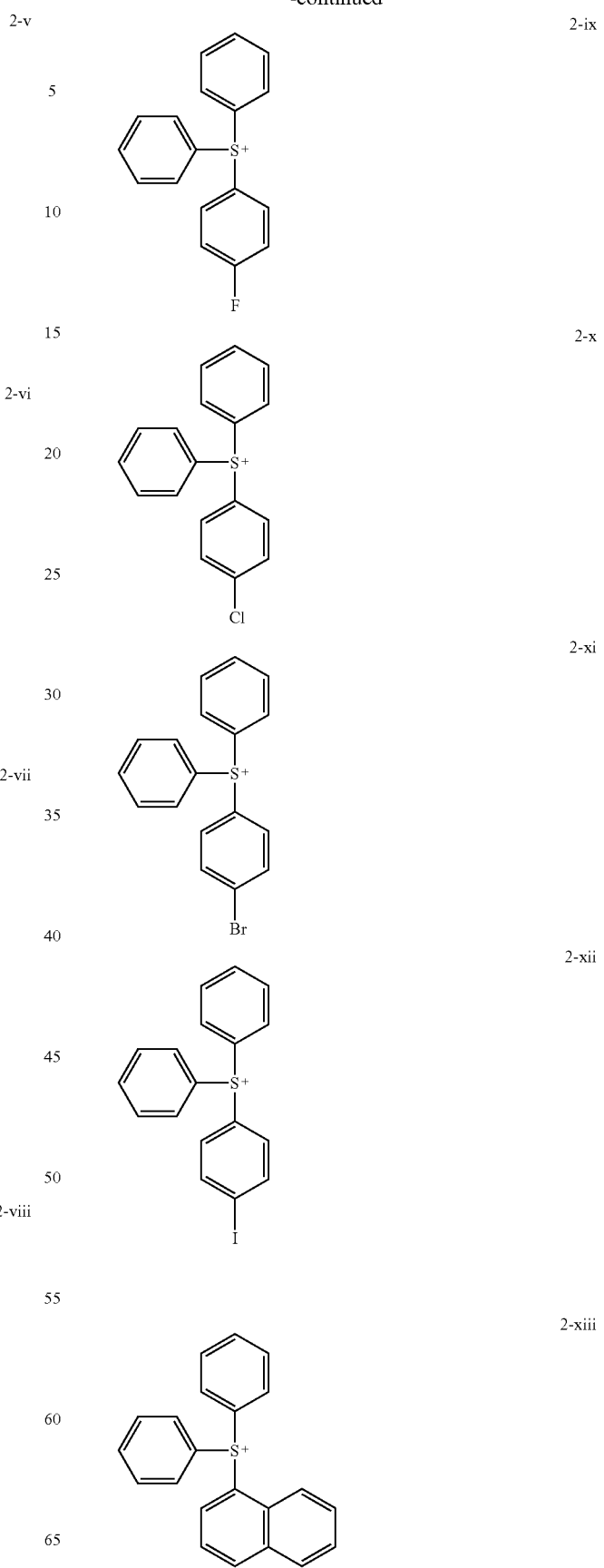

2-xiv
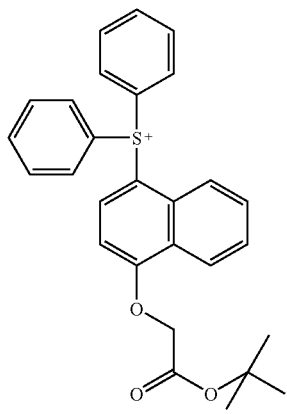
2-xv
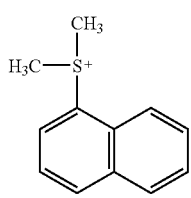
2-xvi
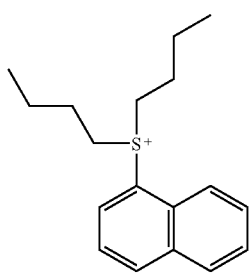
2-xvii
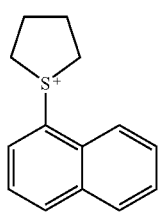
2-xviii
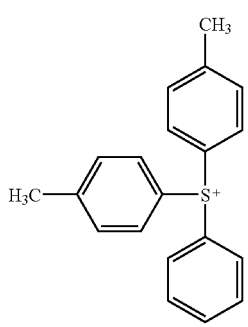
2-xix
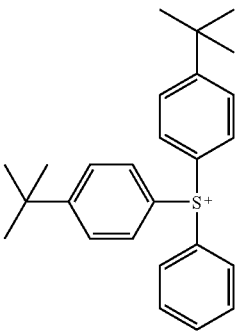
2-xx
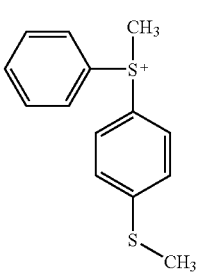
The compounds of the formula (3A) and formula (3B) may be more specifically compounds represented by the following formulas (3-i) to (3-ix):
3-i
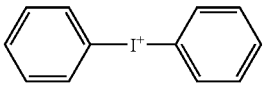
3-ii
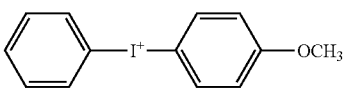
3-iii
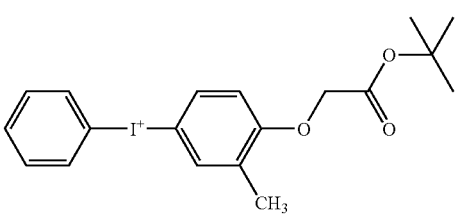
3-iv
3-v
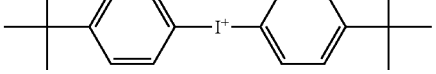
3-vi
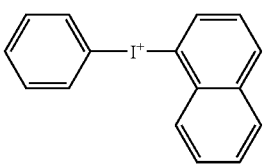
3-vii
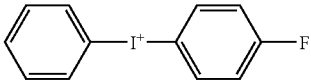

-continued

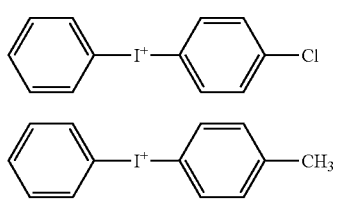

According to another embodiment of the invention, the acid generator according to the present invention may be more specifically a salt represented by the following formula (4A), formula (4B), formula (4C) or formula (4D):

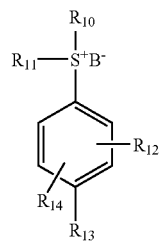

[Formula 4A]

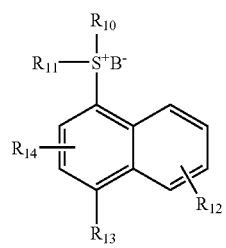

[Formula 4B]

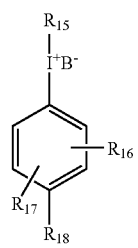

[Formula 4C]

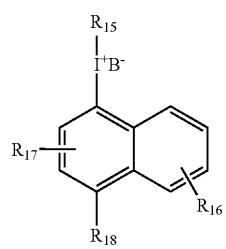

[Formula 4D]

wherein $R_{10}$, $R_{11}$ and $R_{15}$ each independently represent an alkyl group having 1 to 12 carbon atoms, an allyl group having 2 to 12 carbon atoms, a perfluoroalkyl group having 1 to 12 carbon atoms, a benzyl group or an aryl group having 5 to 20 carbon atoms;

$R_{12}$, $R_{13}$, $R_{14}$, $R_{16}$, $R_{17}$ and $R_{18}$ each independently represent a hydrogen atom, an alkyl group having 1 to 12 carbon atoms, a halogen atom, an alkoxy group having 1 to 12 carbon atoms, an aryl group having 5 to 20 carbon atoms, a thiophenoxy group, a thioalkoxy group having 1 to 12 carbon atoms, or an alkoxycarbonylmethoxy group having 1 to 6 carbon atoms; and B represents any one of the following formula (5) to formula (13):

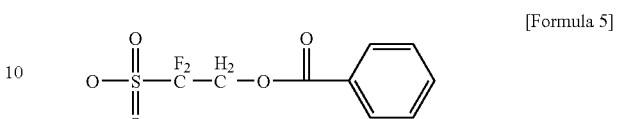

[Formula 5]

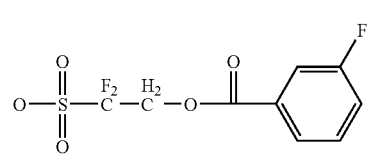

[Formula 6]

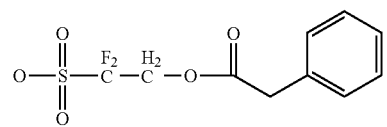

[Formula 7]

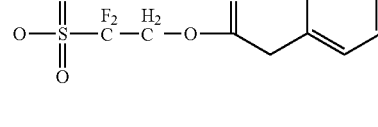

[Formula 8]

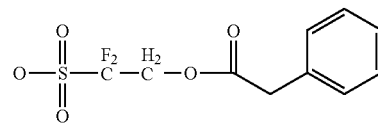

[Formula 9]

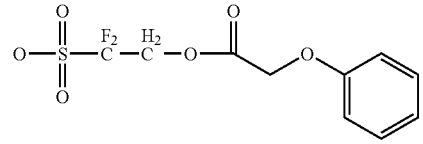

[Formula 10]

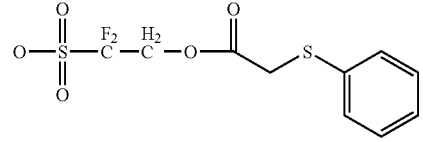

[Formula 11]

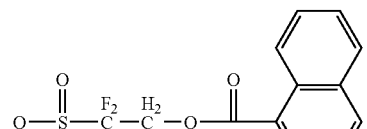

[Formula 12]

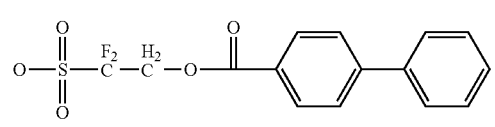

[Formula 13]

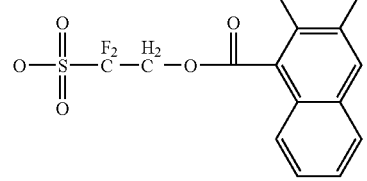

The present invention also provides a method for producing the acid generator represented by the formula (1).

Hereinafter, the method for producing the acid generator represented by formula (1) of the invention will be described.

The compound for formula (1) can be produced by a reaction between a salt represented by the following formula (14) and a compound represented by the following formula (15):

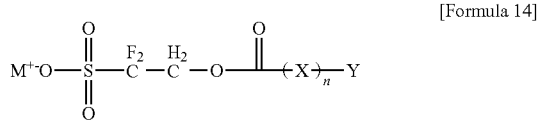

[Formula 14]

wherein X represents an alkyl group having 1 to 10 carbon atoms, —$X_1$—O—$X_2$— or a heteroatom selected from the group consisting of N, S and F; $X_1$ and $X_2$ each independently represent an alkylene group having 1 to 10 carbon atoms; Y represents a cyclic hydrocarbon group having 5 to 30 carbon atoms and containing one or more aromatic rings, while one or more hydrogen atoms on the ring of the cyclic hydrocarbon group may be substituted by one or more members selected from the group consisting of —O—$Y_1$, —CO—$Y_2$, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group and a cyano group; $Y_1$ and $Y_2$ each independently represent an alkyl group having 1 to 6 carbon atoms; M represents Li, Na or K; and n represents an integer of 0 or 5;

$$A^+Z^-$$ [Formula 15]

wherein Z represents $OSO_2CF_3$, $OSO_2C_4F_9$, $OSO_2C_8F_{17}$, $N(CF_3)_2$, $N(C_2F_5)_2$, $N(C_4F_9)_2$, $C(CF_3)_3$, $C(C_2F_5)_3$, $C(C_4F_9)_3$, F, Cl, Br, I, $BF_4$, $ASF_6$ or $PF_6$; and $A^+$ represents an organic counterion.

According to an embodiment of the present invention, the acid generator of the formula (1) of the invention can be produced by reacting the salt of formula (14) and the compound of formula (15) at a temperature of 0 to 100° C., using a solvent formed by mixing water with an organic solvent such as dichloromethane, chloroform or dichloroethane.

Preferably, the amount of use of the salt of formula (14) is about 1 mole to 2 moles per mole of the compound of formula (15). If the obtained salt of formula (14) is solid, the salt is purified by a recrystallization method, or a solidification method using a mixture of a good solvent and a poor solvent for the salt. If the salt of formula (14) is oil, the salt may be purified by extraction or concentration.

The salt of formula (14) can also be produced by reacting an alcohol compound of the following formula (16) with a carbonyl chloride compound of the following formula (17):

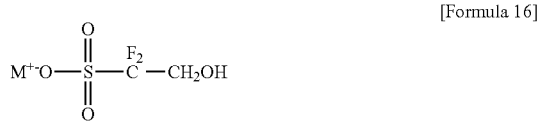

[Formula 16]

wherein M represents Li, Na or K;

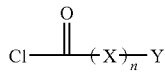

[Formula 17]

wherein X represents a monocyclic or polycyclic hydrocarbon group having 3 to 30 carbon atoms, while at least one or more hydrogen atoms on the monocyclic or polycyclic hydrocarbon group may be substituted by an alkyl or alkoxy group having 1 to 10 carbon atoms, the alkyl or alkoxy group being unsubstituted or substituted with an ether group, an ester group, a carbonyl group, an acetal group, an epoxy group, a nitrile group or an aldehyde group, or by a perfluoroalkyl group having 1 to 4 carbon atoms, a hydroxyalkyl group having 1 to 10 carbon atoms or a cyano group;

Y represents a phenyl group, a naphthyl group, an anthryl group, a phenanthrenyl group, a fluorenyl group or a pyrene group, while one or more hydrogen atoms on these rings may be substituted by one or more members selected from the group consisting of —O—$Y_1$, —CO—$Y_2$, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group and a cyano group; and $Y_1$ and $Y_2$ each independently represent an alkyl group having 1 to 6 carbon atoms.

Specifically, according to the method involving such reaction, generally the alcohol of formula (16) and the carbonyl chloride of formula (17) are dissolved in a reaction solvent such as dichloromethane, chloroform, dichloroethane, acetonitrile or toluene at a temperature of 0 to 100° C., and then a basic catalyst such as triethylamine, diethylamine, pyridine or diethylisopropylamine is added in an amount of about 1 mole to 2 moles per mole of the alcohol of formula (16). N,N-dimethylaminopyridine can also be used as a catalyst, in an amount of about 0.1 moles to 0.5 moles per mole of the alcohol of formula (16).

The alcohol compound of formula (16) can be produced by dissolving an ester compound represented by the following formula (18) in an alcoholic solvent, and then adding a reducing agent dropwise:

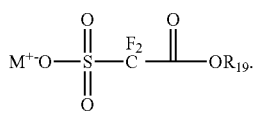

[Formula 18]

wherein $R_{19}$ represents one selected from the group consisting of hydrogen, methyl, trifluoromethyl, trichloromethyl, tribromomethyl and triiodomethyl; and M represents Li, Na or K.

To describe the method for producing the alcohol of formula (16) more specifically, an ester compound such as that represented by the formula (18) is dissolved using an alcoholic solvent such as tetrahydrofuran, methanol, ethanol or propanol, and then in an ice bath, a reducing agent such as sodium borohydride ($NaBH_4$) is slowly added dropwise. When the dropwise addition is completed, the reaction mixture is stirred for about 4 hours in an oil bath at 60° C., and then the reaction mixture is quenched with distilled water, followed by removal of the solvent. The reaction mixture having removed of the solvent is dissolved again in distilled water, and then the solution is acidified using concentrated hydrochloric acid until the pH value reaches 5 to 6. The resulting mixture liquid is concentrated, and then methanol is added to make the mixture in a slurry state. The slurry is filtered, and the filtrate is washed using hexane, concentrated again, and crystallized from diethyl ether. The crystals are filtered and dried to yield the desired alcohol, such as the compound of formula (16).

As for the reducing agent, lithium aluminum hydride (LiAlH$_4$), BH$_3$-THF, NaBH$_4$—AlCl$_3$, NaBH$_4$—LiCl and LiAl(OMe)$_3$ can also be used, in addition to sodium borohydride, and these agents may be used individually alone or as mixtures.

The acid generator according to the present invention has a characteristic that the diffusion rate of acid, the distance of diffusion, acidity and transmissibility at the time of using an ArF light source can be appropriately controlled by introducing an anion group containing an aromatic ring into the molecule of the acid generator. Thus, the acid generator is suitable for the use in chemically amplified resist compositions.

The present invention also provides a chemically amplified resist composition containing the acid generator according to the present invention. The chemically amplified resist composition may also contain, in addition to the acid generator according to the invention, various conventionally used additives such as polymers, effluence suppressants, basic additives, defoaming agents, surfactants, acid diffusion controlling agents and adhesive aids, and solvents.

The present invention will be specifically described with reference to the following Synthesis Examples and Examples. However, the present invention is not intended to be limited to these Synthesis Examples and Examples.

Synthesis Example 1

Benzoic acid 2,2-difluoro-2-sulfoethyl ester diphenylmethylphenylsulfonium salt

<1> 83 g of difluorosulfoacetic acid ethyl ester sodium salt was dissolved in 160 ml of methanol and 1.2 L of tetrahydrofuran (THF) in an ice bath, and 44 g of sodium borohydride (NaBH$_4$) was slowly added dropwise. After the dropwise addition, the ice bath was removed, and the mixture was heated and stirred for about 4 hours at 60° C. After the reaction, the reaction mixture was quenched with distilled water, and then the solvent was removed. The crude reaction mixture was dissolved again in distilled water, and acidified with concentrated hydrochloric acid until the pH value reached 5. The resulting mixture was concentrated, and then methanol was added to obtain a slurry. The slurry was filtered to remove organic salts, and the filtrate was washed two times with hexane. The methanol layer was concentrated again, and then was crystallized from diethyl ether. White solids obtained by filtering the crystals were dried in a vacuum, to obtain 68.5 g (yield 95%) of difluorohydroxyethanesulfonic acid sodium salt was obtained. The structure of the obtained product was confirmed by $^1$H-NMR.

$^1$H-NMR (D$_2$O): d (ppm) 4.18 (t, 2H)

[Reaction Scheme 1]

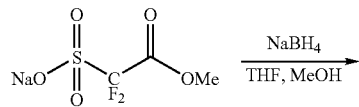

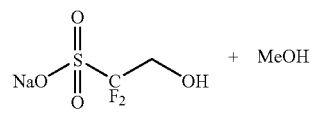

+ MeOH

<2> 10 g of the difluorohydroxyethanesulfonic acid sodium salt produced as described above, and 11.5 g of benzoyl chloride were dissolved in 150 ml of dichloroethane, and the solution was stirred at ambient temperature. 11 g of triethylamine was slowly added dropwise at ambient temperature, and then the reaction temperature was increased to ambient temperature, at which temperature the reaction mixture was stirred for 2 hours.

After completion of the reaction, the reaction solvent was removed, and ethyl ether was added to form a slurry. The slurry was filtered, and then the residue was washed using distilled water and ethyl ether, and dried in a vacuum. Thus, 11.5 g (yield 73.5%) of benzoyloxymethyldifluorosulfonic acid sodium salt having a structure as shown in the following reaction scheme 2 was obtained, and the structure of the product was confirmed by $^1$H-NMR (see FIG. 1).

$^1$H-NMR (dimethylsulfoxide-d$_6$, internal standard: tetramethylsilane): d (ppm), 4.80 (t, 2H), 7.54-7.90 (m, 3H), 8.00 (d, 2H)

[Reaction Scheme 2]

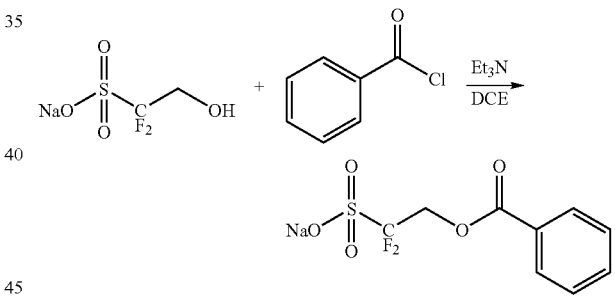

Figure 2:
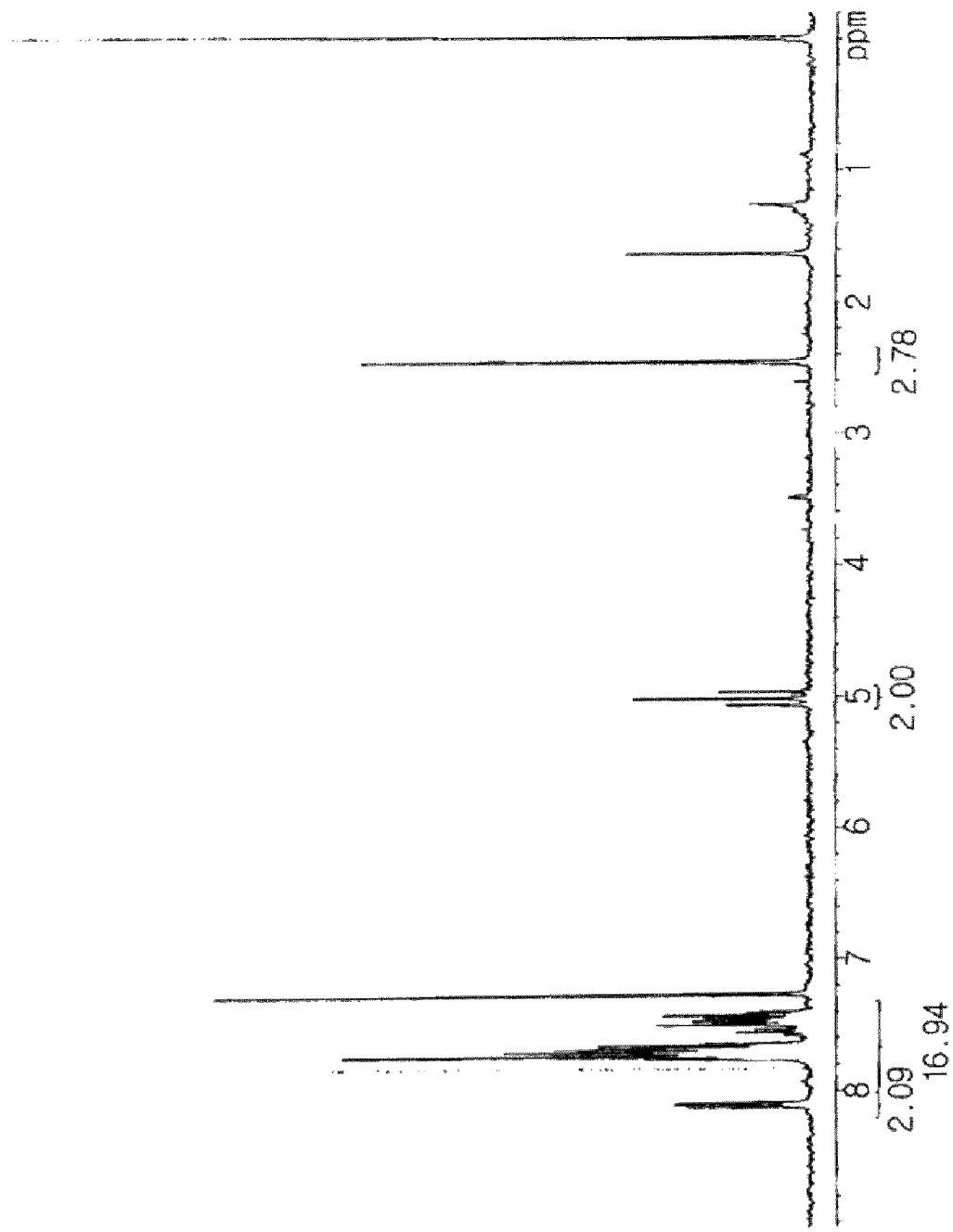
FIG. 2 is a $^1$H-NMR spectrum of a compound produced according to another embodiment of the present invention.

<3> 4 g of the benzoyloxymethyldifluorosulfonic acid sodium salt produced as described in <2>, and 4.22 g of diphenylmethylphenylsulfonium trifluoromethanesulfonic acid sodium salt were dissolved in 40 ml of dichloromethane and 40 ml of water, and the mixture was stirred vigorously for 3 hours to carry out a two-layer reaction. After completion of the stirring, a small portion of the organic layer was removed, and the progress of the reaction was confirmed by $^{19}$F-NMR. When the reaction was completed, the organic layer was collected, and the solvent was removed. The residue was washed using dichloromethane, which is a good solvent, and hexane, which is a poor solvent. The solvent was removed, and the residue was dried under reduced pressure to obtain 3.2 g (yield 59.5%) of benzoic acid 2,2-difluoro-2-sulfoethyl ester diphenylfluorophenylsulfonium salt. The structure of the product was confirmed by $^1$H-NMR (see FIG. 2).

$^1$H-NMR (chloroform-d$_3$, internal standard: tetramethylsilane): d (ppm) 2.45 (s, 3H), 5.01 (t, 2H), 7.42-7.90 (m, 17H), 8.10 (d, 2H)

[Reaction Scheme 3]

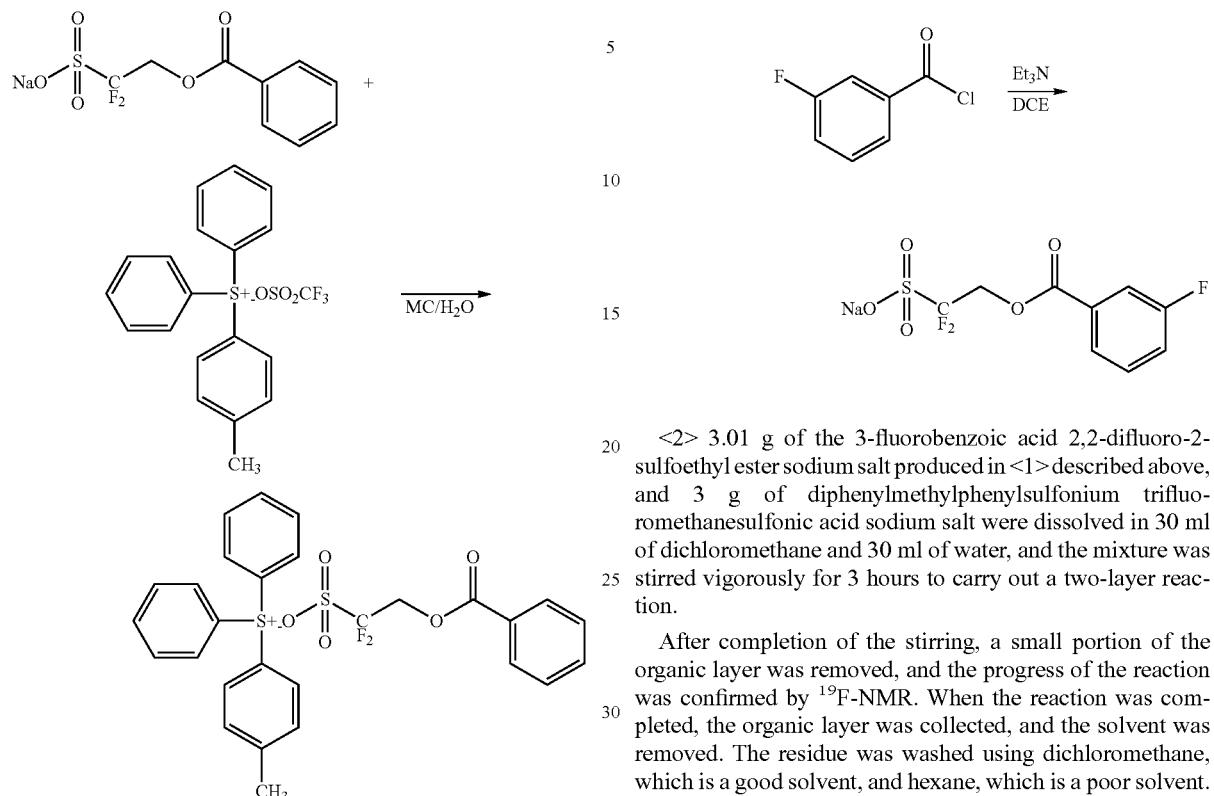

Synthesis Example 2

<1> 10 g of the difluorohydroxyethanesulfonic acid sodium salt produced in <1> of Synthesis Example 1, and 12.8 g of 3-fluorobenzoyl chloride were dissolved in 150 ml of dichloroethane, and the solution was stirred at ambient temperature. 15.05 ml of triethylamine was slowly added dropwise at ambient temperature, and then the reaction temperature was raised to 60° C., at which temperature, the reaction mixture was stirred for 2 hours.

Figure 3:
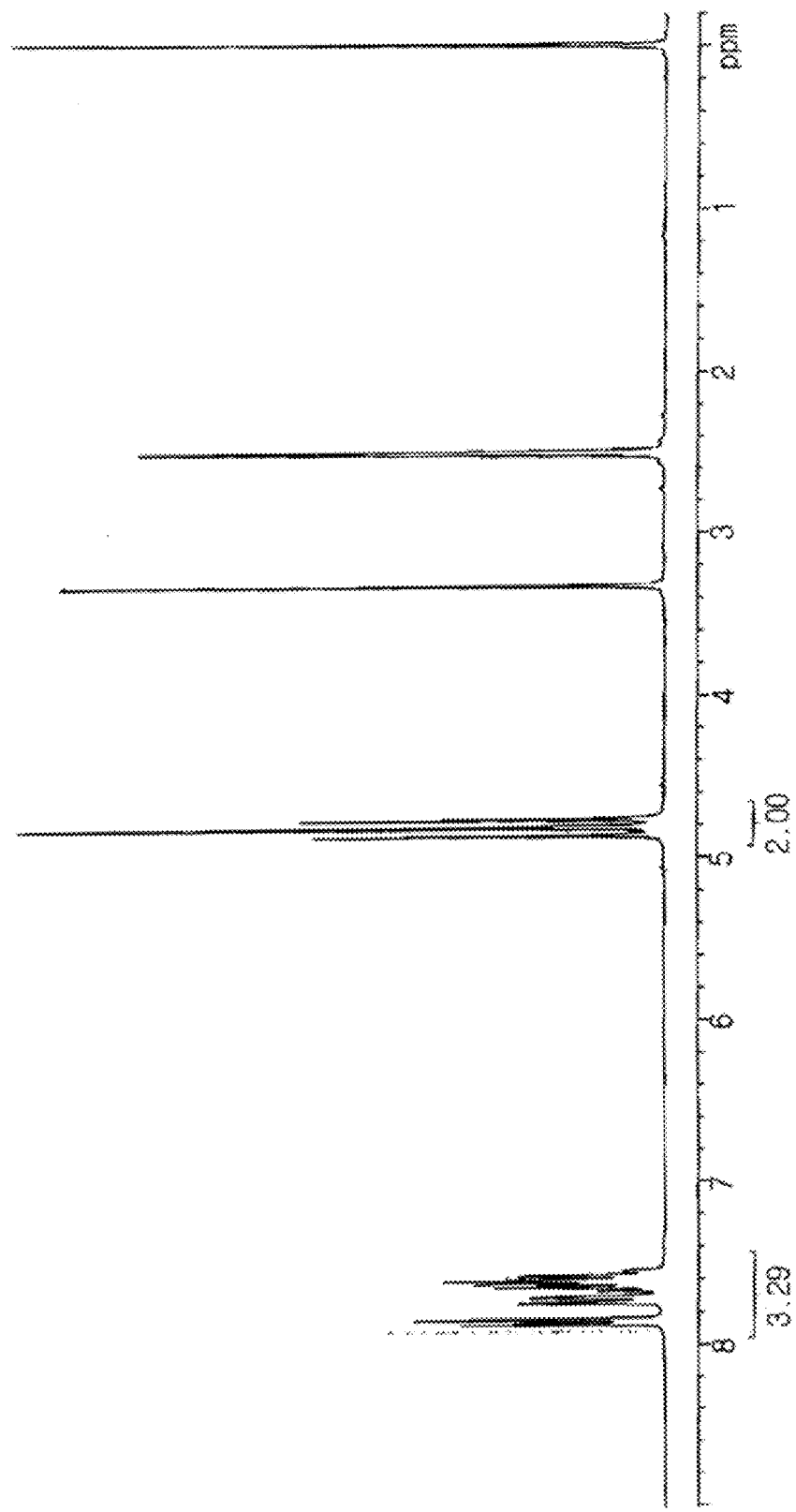
FIG. 3 is a $^1$H-NMR spectrum of a compound produced according to another embodiment of the present invention.

After completion of the reaction, the reaction solvent was removed, and ethyl ether was added to form a slurry. The slurry was filtered, and then the residue was washed using distilled water and ethyl ether, and dried in a vacuum, to obtain 13.5 g (yield 81.8%) of 3-fluorobenzoic acid 2,2-difluoro-2-sulfoethyl ester sodium salt having a structure as shown in the following reaction scheme 4. The structure of the product was confirmed by $^1$H-NMR (see FIG. 3).

$^1$H-NMR (dimethylsulfoxide-d$_6$, internal standard: tetramethylsilane): d (ppm) 4.81 (t, 2H), 7.57-7.87 (m, 4H)

[Reaction Scheme 4]

<2> 3.01 g of the 3-fluorobenzoic acid 2,2-difluoro-2-sulfoethyl ester sodium salt produced in <1> described above, and 3 g of diphenylmethylphenylsulfonium trifluoromethanesulfonic acid sodium salt were dissolved in 30 ml of dichloromethane and 30 ml of water, and the mixture was stirred vigorously for 3 hours to carry out a two-layer reaction.

Figure 4:
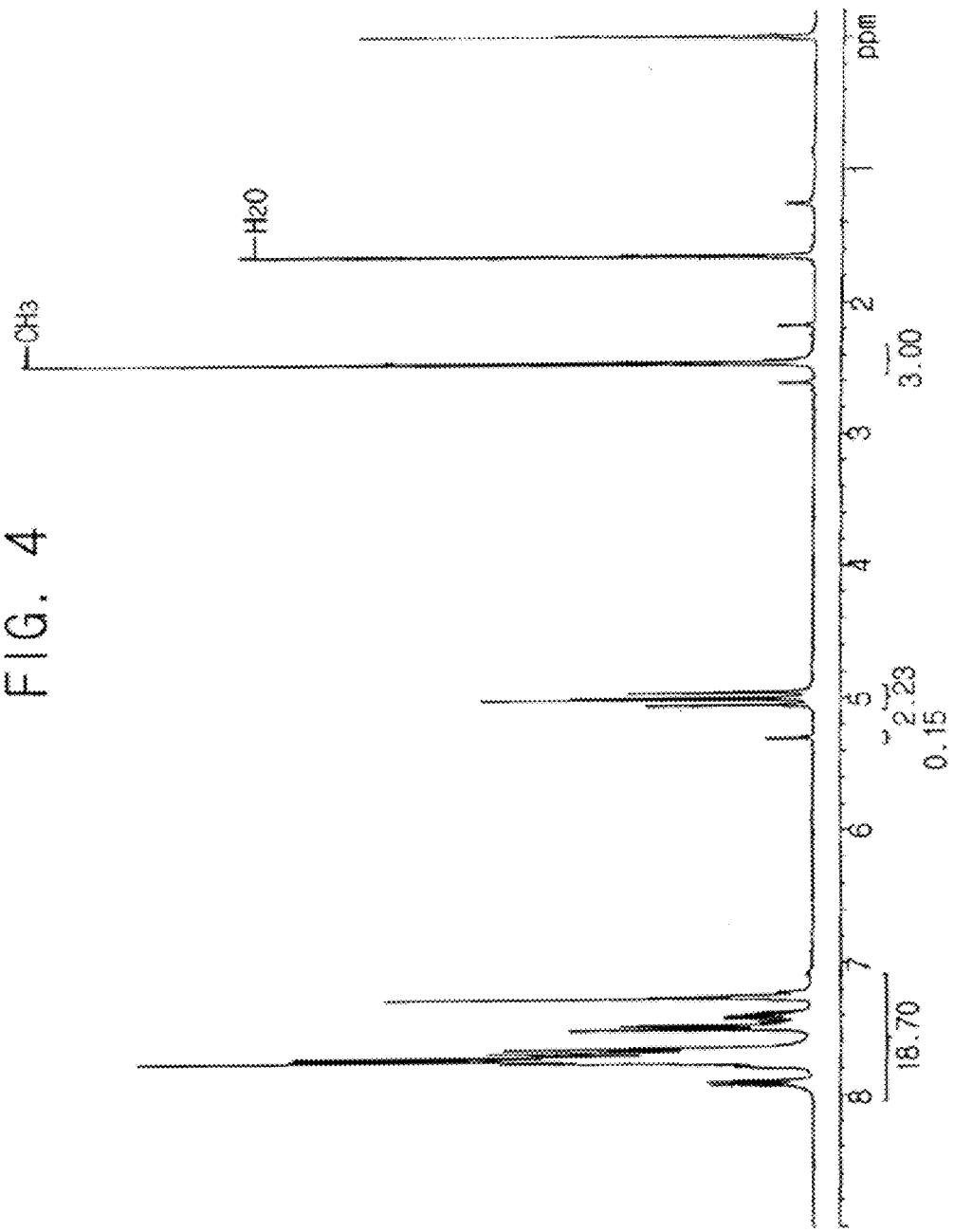
FIG. 4 is a $^1$H-NMR spectrum of a compound produced according to another embodiment of the present invention.

After completion of the stirring, a small portion of the organic layer was removed, and the progress of the reaction was confirmed by $^{19}$F-NMR. When the reaction was completed, the organic layer was collected, and the solvent was removed. The residue was washed using dichloromethane, which is a good solvent, and hexane, which is a poor solvent. The solvent was removed, and the residue was dried under reduced pressure to obtain 3.53 g (yield 90.05%) of 3-fluorobenzoic acid 2,2-difluoro-2-sulfoethyl ester diphenylmethylphenylsulfonium salt. The structure of the product was confirmed by $^1$H-NMR (see FIG. 4).

$^1$H-NMR (chloroform-d$_3$, internal standard: tetramethylsilane): d (ppm) 2.46 (t, 3H), 5.00 (t, 2H), 7.25-7.89 (m, 18H)

[Reaction Scheme 5]

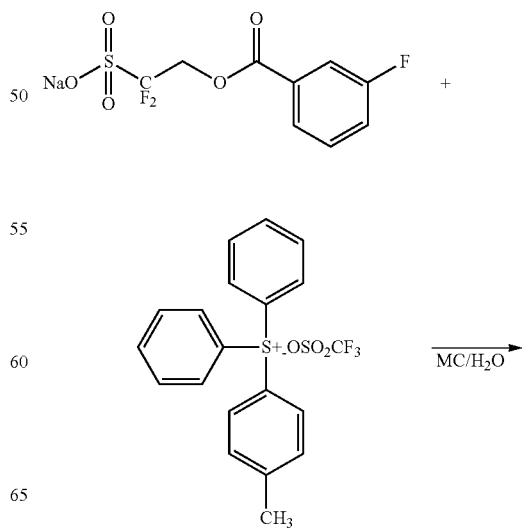

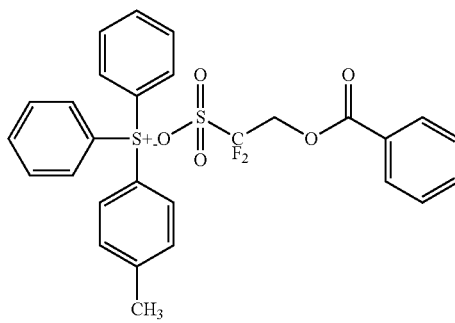

Synthesis Example 3

Figure 5:
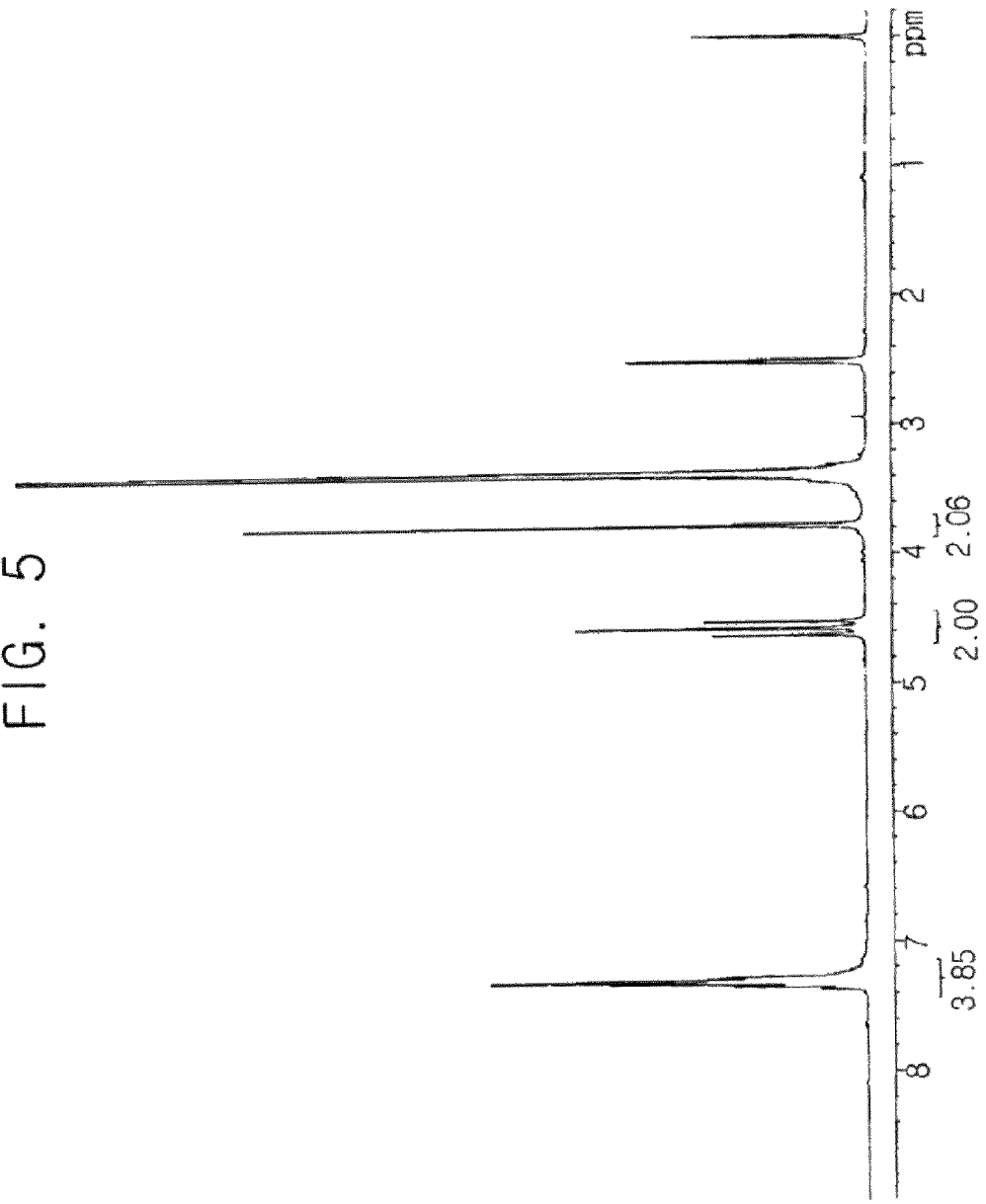
FIG. 5 is a $^1$H-NMR spectrum of a compound produced according to another embodiment of the present invention.

<1> The reaction described in <2> of Synthesis Example 1 was performed under the same conditions, except that phenylacetyl chloride (10.8 ml) was used instead of benzoyl chloride as the reactant to react with alcohol, and thus 7.6 g (yield 46.6%) of phenylacetyloxymethyl difluoromethanesulfonic acid sodium salt as shown in the following reaction scheme 6 was obtained. The structure of the product was confirmed by $^1$H-NMR (see FIG. 5).

$^1$H-NMR (dimethylsulfoxide-$d_6$, internal standard: tetramethylsilane): d (ppm) 4.58 (t, 3H), 7.21-7.38 (m, 5H)

[Reaction Scheme 6]

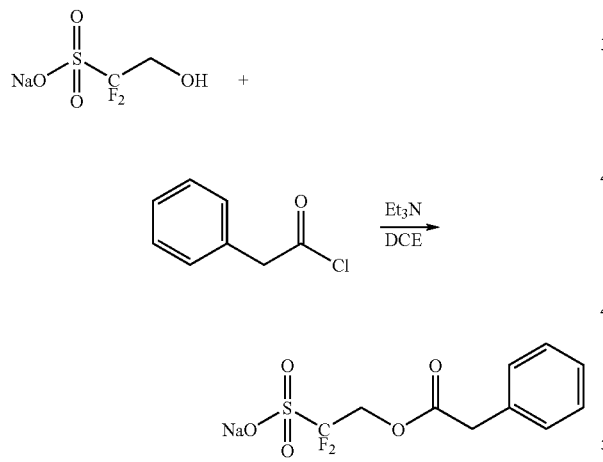

Figure 6:
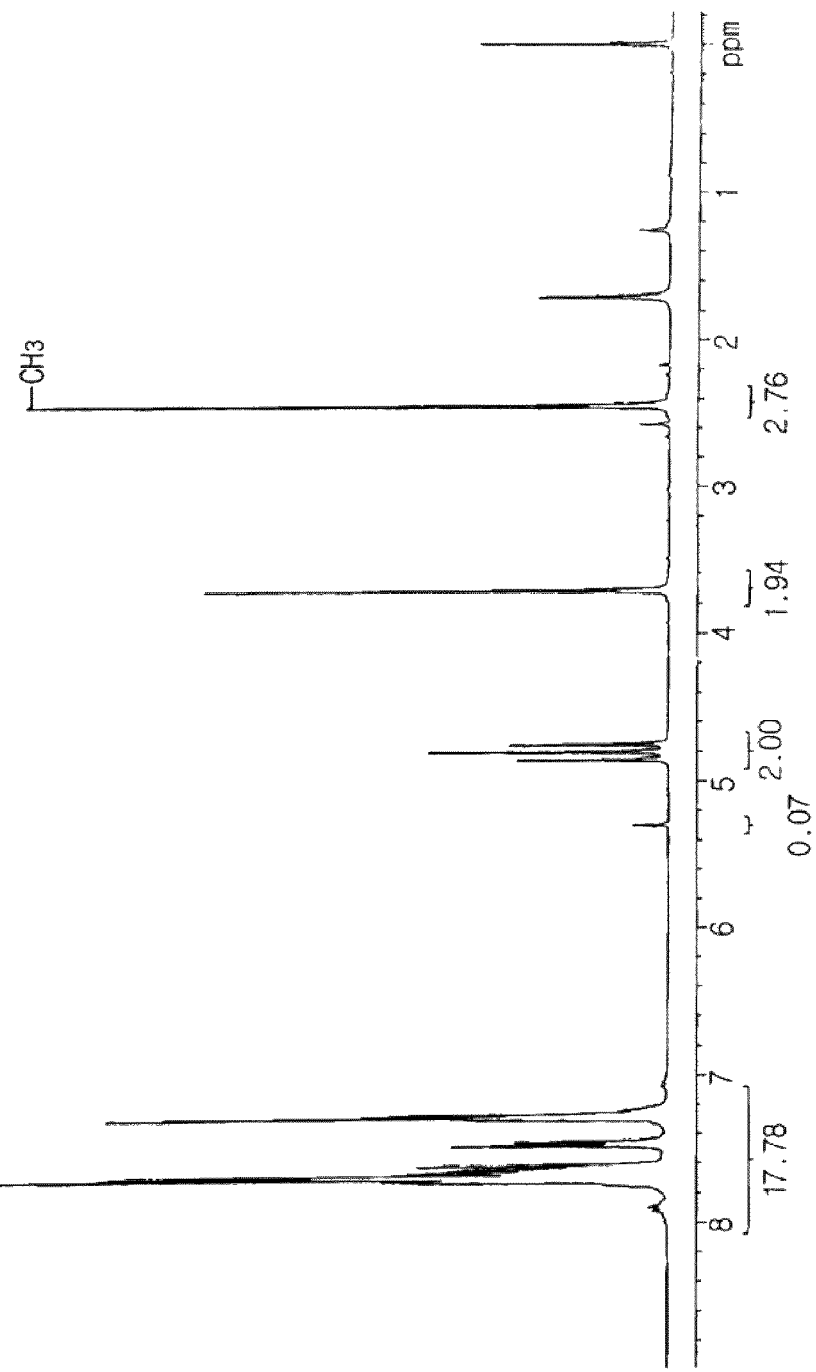
FIG. 6 is a $^1$H-NMR spectrum of a compound produced according to another embodiment of the present invention.

<2> The reaction described in <3> of Synthesis Example 1 was performed under the same conditions, except that the phenylacetyloxymethyl difluoromethanesulfonic acid sodium salt (2.97 g) produced in <1> above was used instead of the benzoyloxymethyldifluorosulfonic acid sodium salt in the reaction with diphenylmethylphenylsulfonium trifluoromethanesulfonic acid sodium salt, and thus 3.87 g (yield 99.5%) of phenylacetic acid 2,2-difluoro-2-sulfoethyl ester diphenylmethylphenylsulfonium salt as shown in the following reaction scheme 7 was obtained. The structure of the product was confirmed by $^1$H-NMR (see FIG. 6).

$^1$H-NMR (chloroform-$d_3$, internal standard: tetramethylsilane): d (ppm) 2.45 (s, 3H), 3.71 (s, 2H), 4.81 (t, 2H), 7.21-7.92 (m, 19H)

[Reaction Scheme 7]

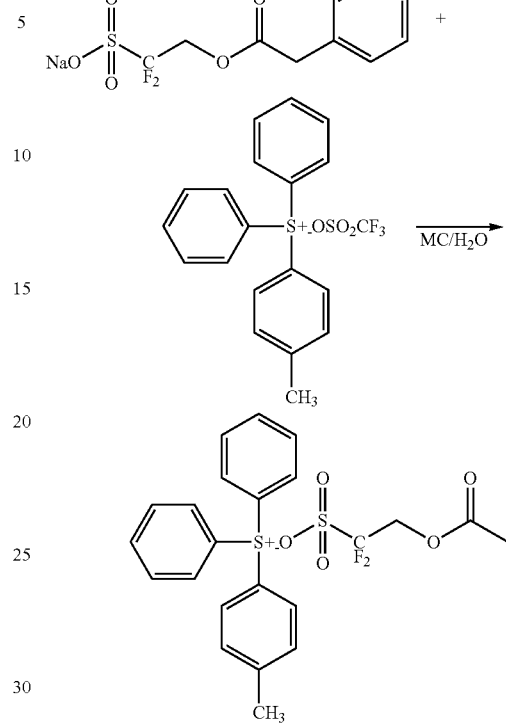

Synthesis Example 4

Figure 7:
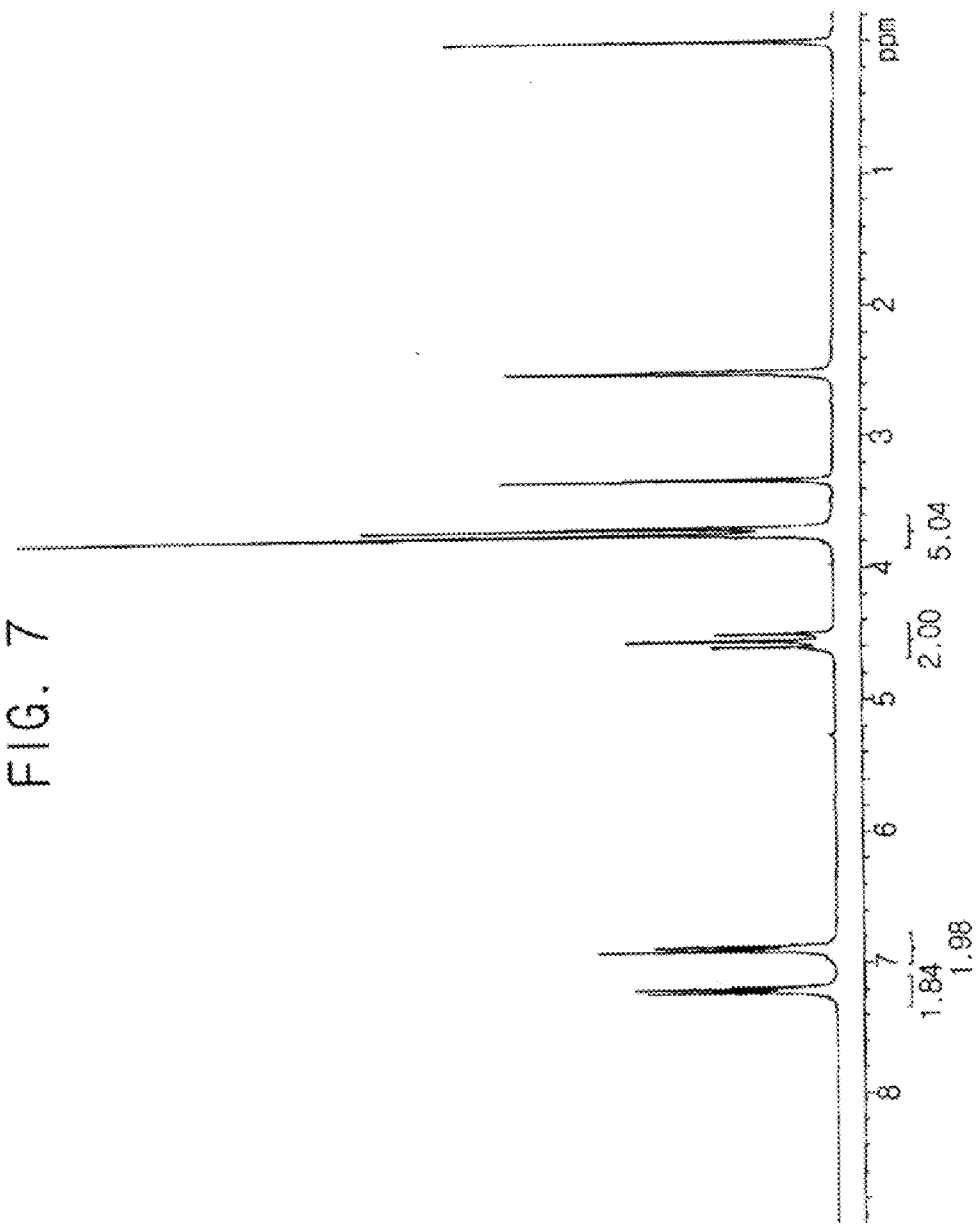
FIG. 7 is a $^1$H-NMR spectrum of a compound produced according to another embodiment of the present invention.

<1> The reaction described in <2> of Synthesis Example 1 was performed under the same conditions, except that 4-methoxyphenylacetyl chloride (10 g) was used instead of benzoyl chloride as the reactant to react with alcohol, and thus 7.1 g (yield 59.4%) of 4-methoxyphenylacetyloxymethyl difluoromethanesulfonic acid sodium salt as shown in the following reaction scheme 8 was obtained. The structure of the product was confirmed by $^1$H-NMR (see FIG. 7).

$^1$H-NMR (dimethylsulfoxide-$d_6$, internal standard: tetramethylsilane): d (ppm) 3.69 (s, 2H), 3.73 (s, 3H), 4.55 (t, 2H), 6.87 (d, 2H), 7.20 (d, 2H)

[Reaction Scheme 8]

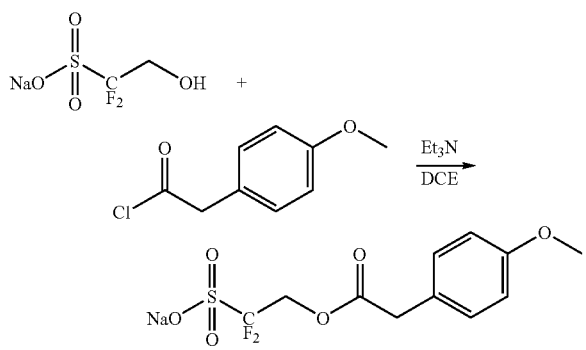

Figure 8:
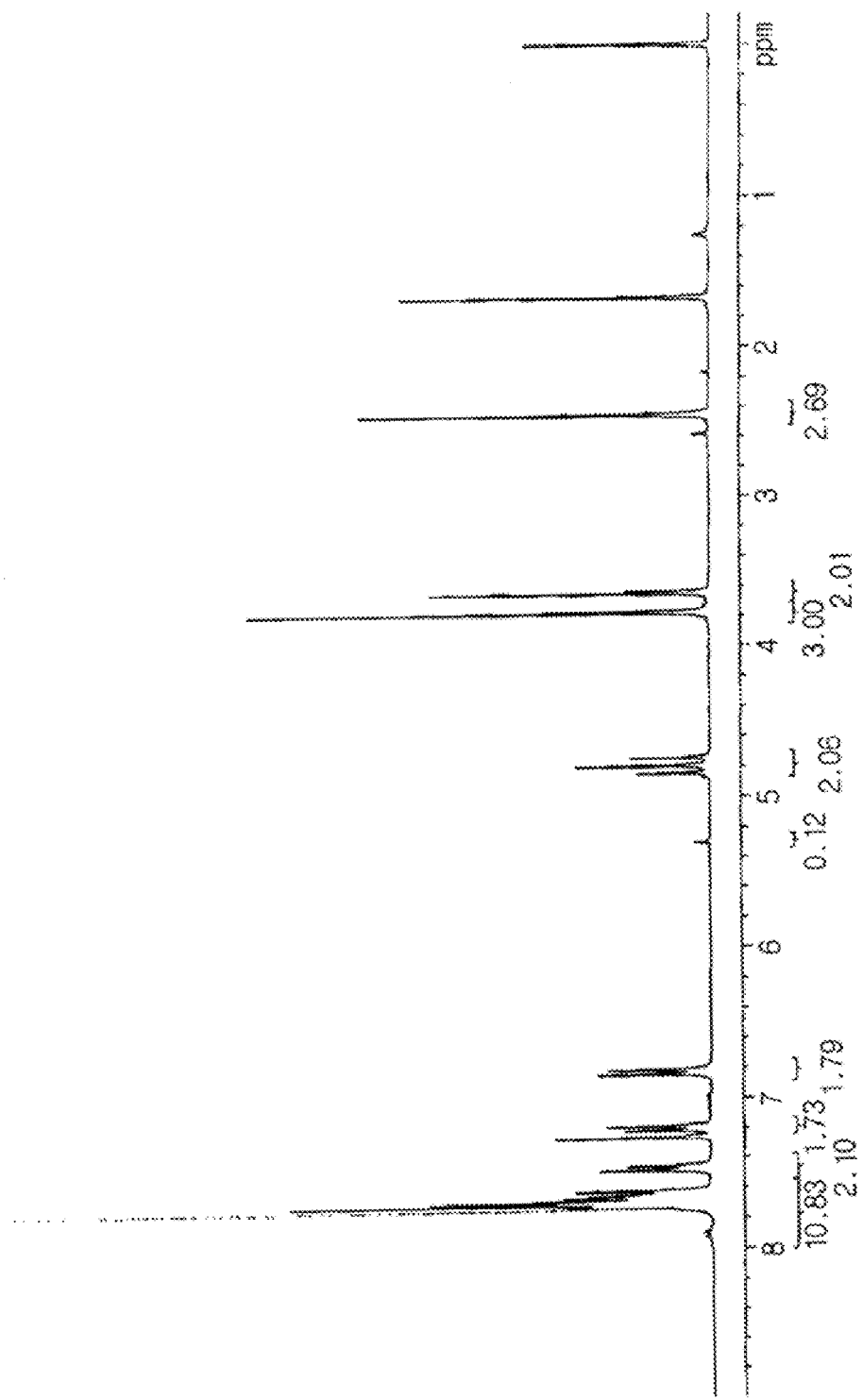
FIG. 8 is a $^1$H-NMR spectrum of a compound produced according to another embodiment of the present invention.

<2> The reaction described in <3> of Synthesis Example 1 was performed under the same conditions, except that the 4-methoxyphenylacetyloxymethyl difluoromethanesulfonic acid sodium salt (0.8 g) produced in <1> of Synthesis Example 4 above was used instead of the benzoyloxymethyldifluorosulfonic acid sodium salt in the reaction with diphenylmethylphenylsulfonium trifluoromethanesulfonic acid sodium salt, and thus 3.95 g (yield 95.9%) of 4-methoxyphenylacetic acid 2,2-difluoro-2-sulfoethyl ester diphenylmethylphenylsulfonium salt as shown in the following reaction scheme 9 was obtained. The structure of the product was confirmed by $^1$H-NMR (see FIG. 8).

$^1$H-NMR (chloroform-$d_3$, internal standard: tetramethylsilane): d (ppm) 2.42 (s, 3H), 3.64 (s, 2H), 3.77 (s, 3H), 4.79 (t, 2H), 6.82 (d, 2H), 7.20 (d, 2H), 7.46 (d, 2H), 7.62-7.72 (m, 12H)

[Reaction Scheme 9]

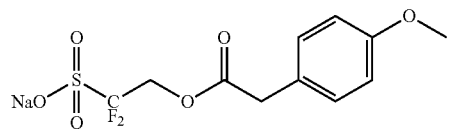

+

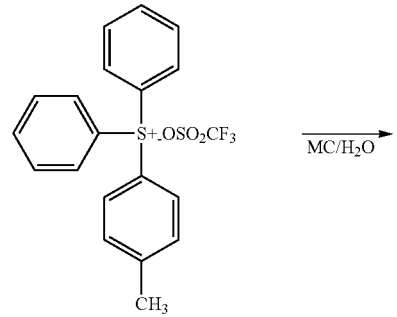

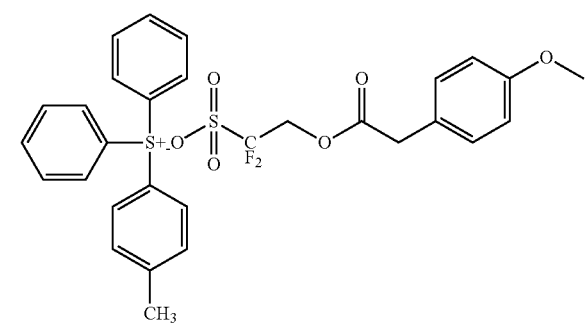

Synthesis Example 5

Figure 9:
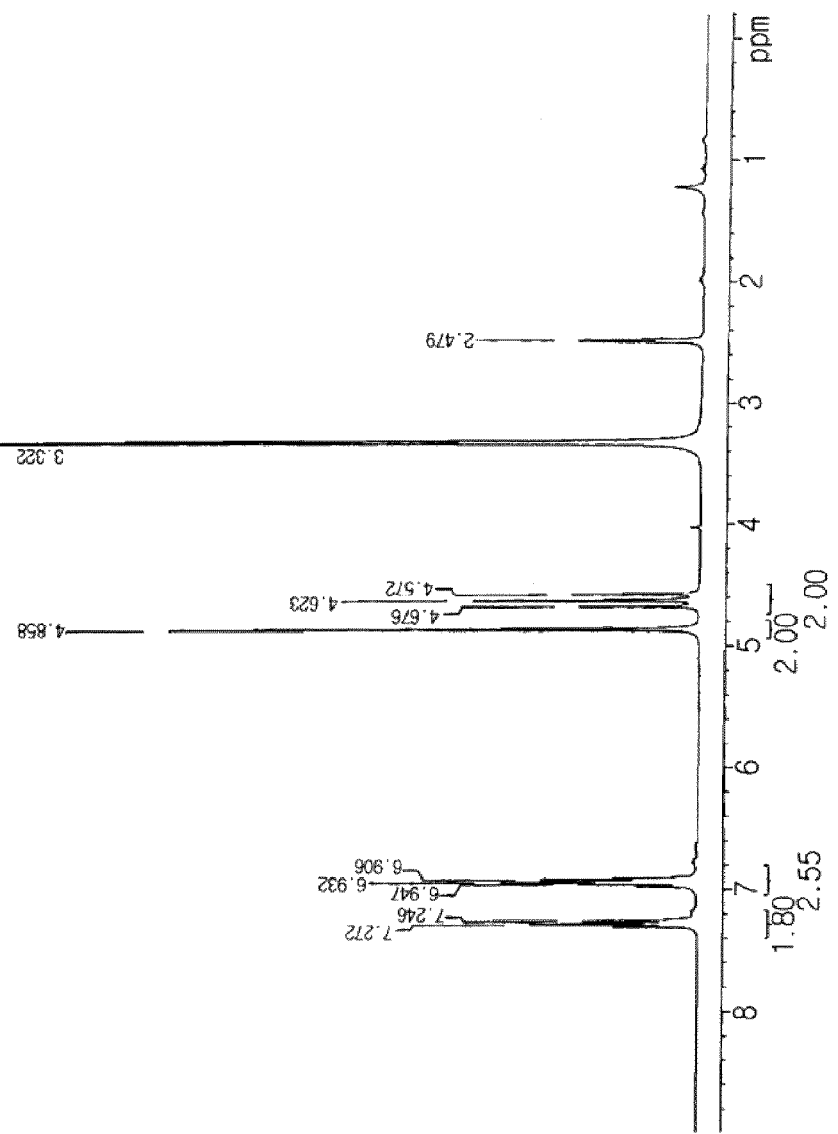
FIG. 9 is a $^1$H-NMR spectrum of a compound produced according to another embodiment of the present invention.

<1> The reaction described in <2> of Synthesis Example 1 was performed under the same conditions, except that phenoxyacetyl chloride (8.98 ml) was used instead of benzoyl chloride as the reactant to react with alcohol, and thus 10 g (yield 87.7%) of phenoxyacetyloxymethyl difluoromethanesulfonic acid sodium salt as shown in the following reaction scheme 10 was obtained. The structure of the product was confirmed by $^1$H-NMR (see FIG. 9).

$^1$H-NMR (dimethylsulfoxide-$d_6$, internal standard: tetramethylsilane): d (ppm) 4.62 (t, 2H), 4.85 (s, 3H), 6.93 (m, 3H), 7.27 (m, 2H)

[Reaction Scheme 10]

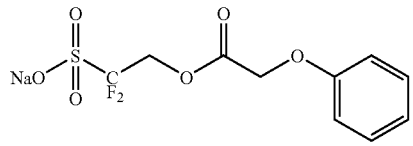

+

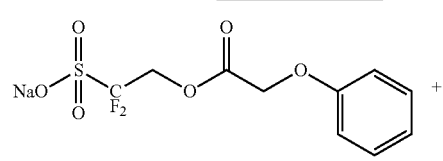

Figure 10:
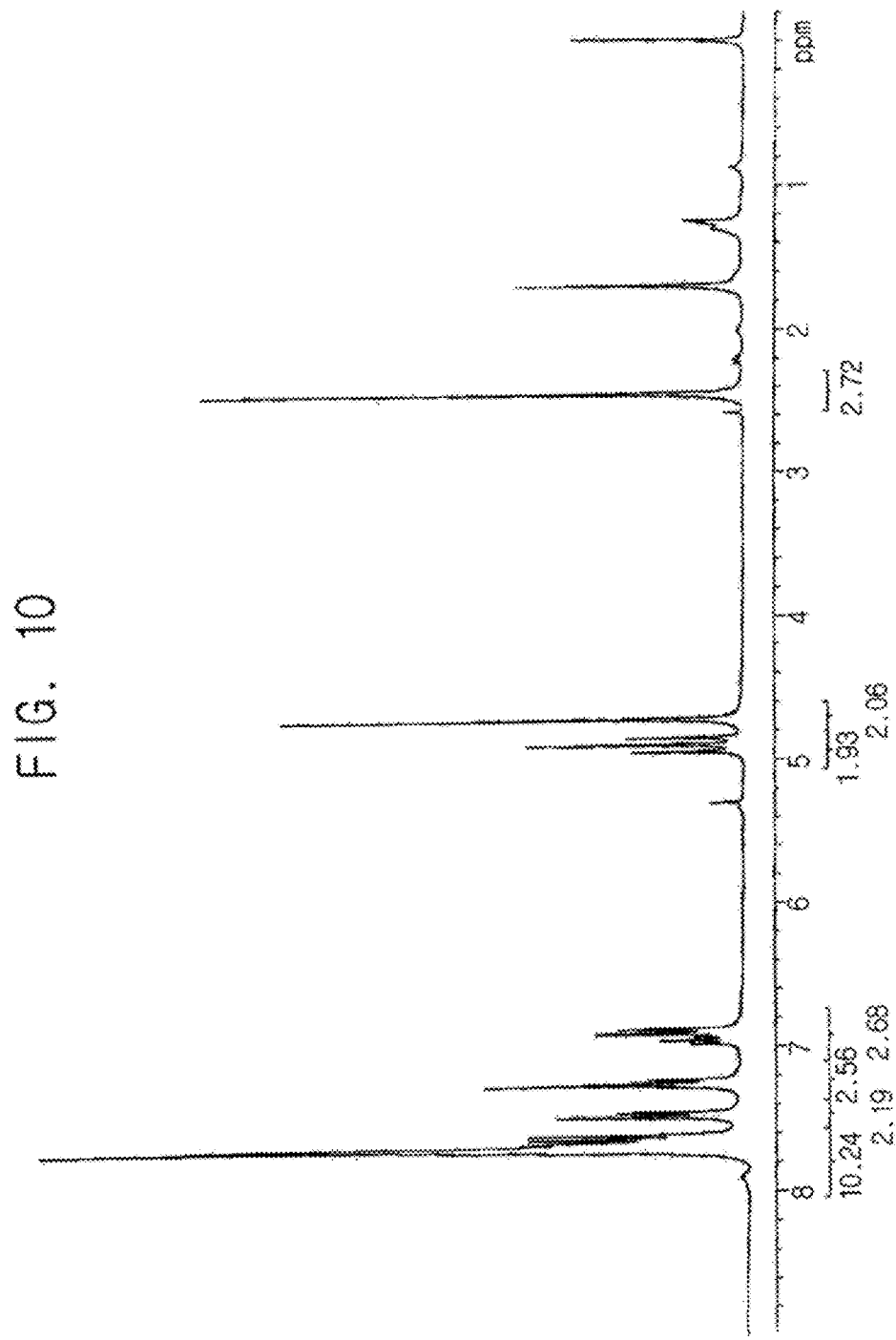
FIG. 10 is a $^1$H-NMR spectrum of a compound produced according to another embodiment of the present invention.

<2> The reaction described in <3> of Synthesis Example 1 was performed under the same conditions, except that the phenoxyacetyloxymethyl difluoromethanesulfonic acid sodium salt (3.66 g) produced in <1> of Synthesis Example 5 above was used instead of the benzoyloxymethyldifluorosulfonic acid sodium salt in the reaction with diphenylmethylphenylsulfonium trifluoromethanesulfonic acid sodium salt, and thus 4.35 g (yield 92.5%) of phenoxyacetic acid 2,2-difluoro-2-sulfoethyl ester diphenylmethylphenylsulfonium salt as shown in the following reaction scheme 11 was obtained. The structure of the product was confirmed by $^1$H-NMR (see FIG. 10).

$^1$H-NMR (chloroform-$d_3$, internal standard: tetramethylsilane): d (ppm) 2.45 (s, 3H), 4.73 (s, 2H), 4.92 (t, 2H), 6.82-7.91 (m, 19H)

[Reaction Scheme 11]

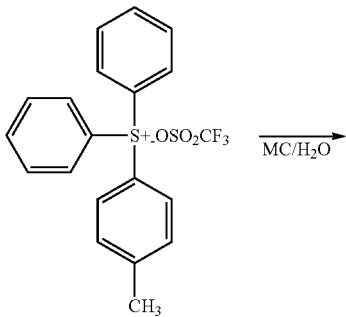

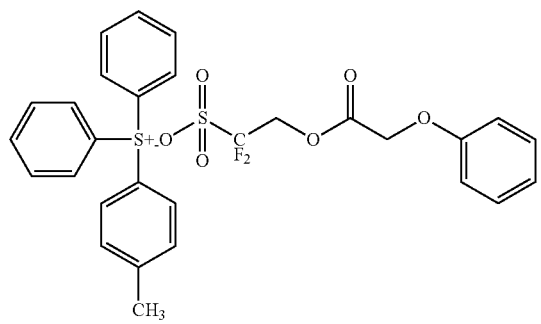

Synthesis Example 6

Figure 11:
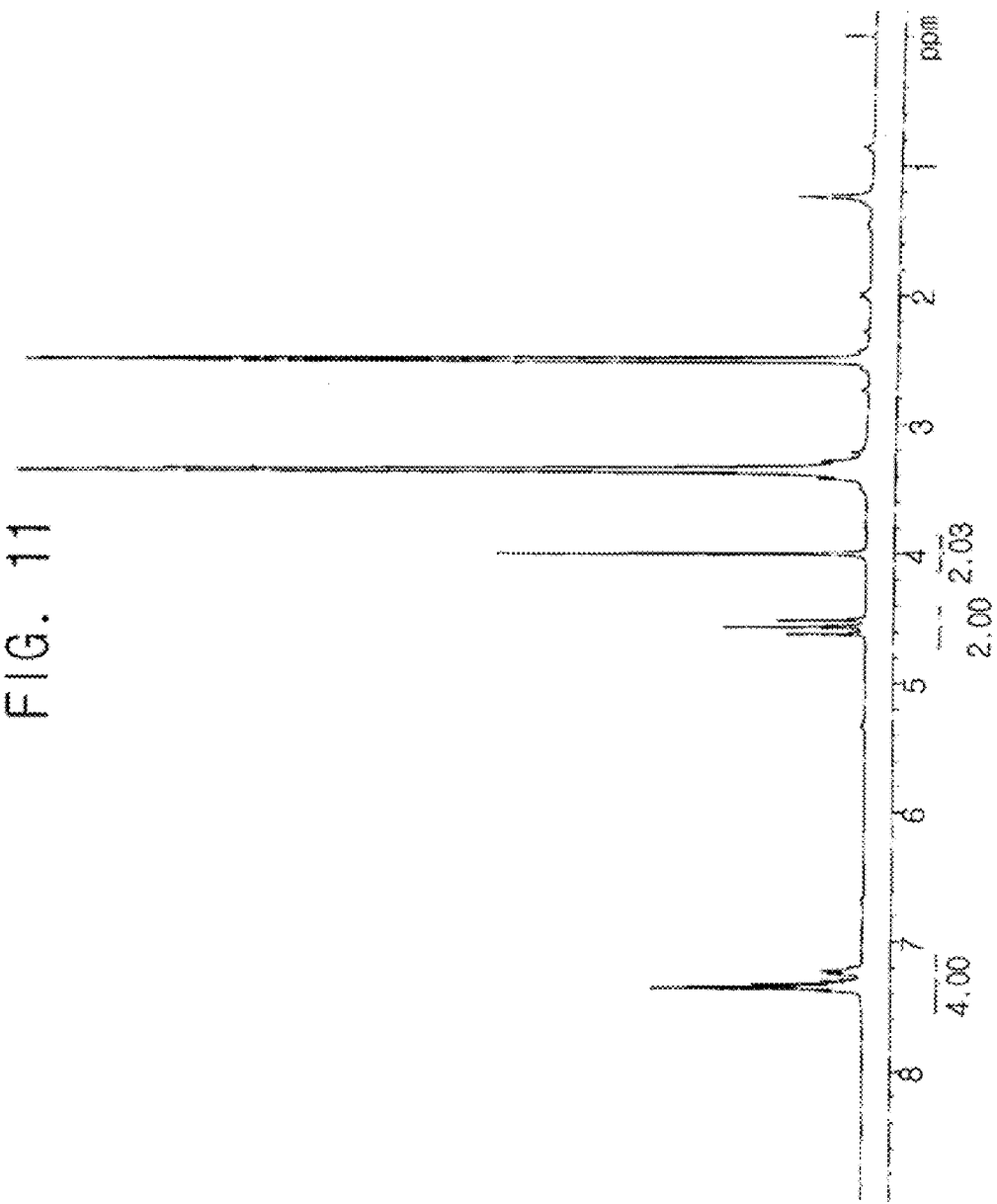
FIG. 11 is a $^1$H-NMR spectrum of a compound produced according to another embodiment of the present invention.

<1> The reaction described in <2> of Synthesis Example 1 was performed under the same conditions, except that phenylthioacetyl chloride (10.6 g) was used instead of benzoyl chloride as the reactant to react with alcohol, and thus 6.87 g (yield 54.1%) of phenylthioacetyloxymethyl difluoromethanesulfonic acid sodium salt as shown in the following reaction scheme 12 was obtained. The structure of the product was confirmed by $^1$H-NMR (see FIG. 11).

$^1$H-NMR (dimethylsulfoxide-$d_6$, internal standard: tetramethylsilane): d (ppm) 3.99 (s, 2H), 4.55 (t, 2H), 7.22-7.37 (m, 5H)

[Reaction Scheme 12]

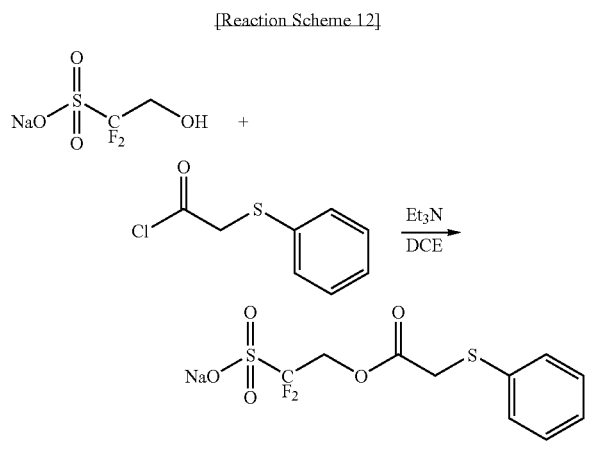

Figure 12:
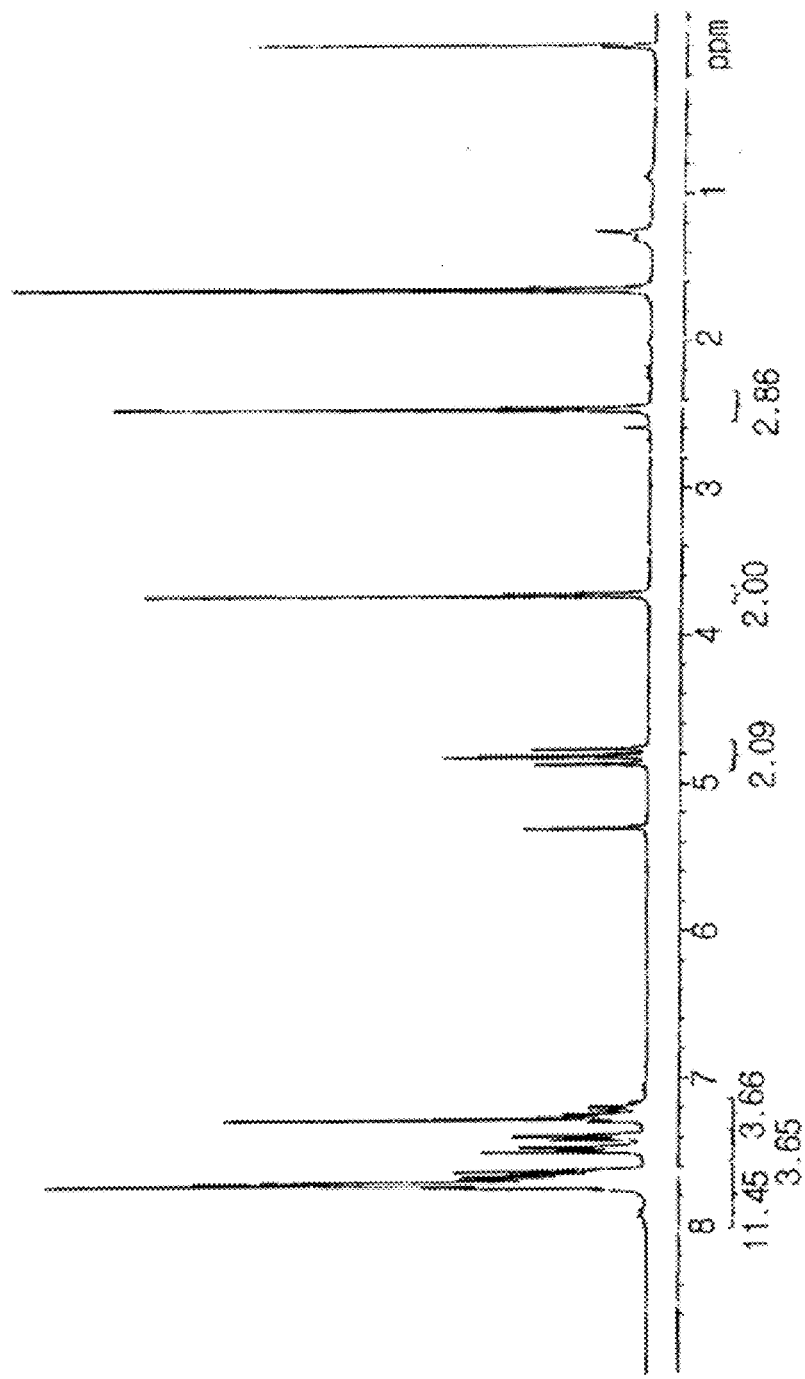
FIG. 12 is a $^1$H-NMR spectrum of a compound produced according to another embodiment of the present invention.

<2> The reaction described in <3> of Synthesis Example 1 was performed under the same conditions, except that the phenylthioacetyloxymethyl difluoromethanesulfonic acid sodium salt (2.5 g) produced in <1> of Synthesis Example 6 above was used instead of the benzoyloxymethyldifluorosulfonic acid sodium salt in the reaction with diphenylmethylphenylsulfonium trifluoromethanesulfonic acid sodium salt, and thus 3.41 g (yield 98%) of phenylthioacetic acid 2,2-difluoro-2-sulfoethyl ester diphenylmethylphenylsulfonium salt as shown in the following reaction scheme 13 was obtained. The structure of the product was confirmed by $^1$H-NMR (see FIG. 12).

$^1$H-NMR (chloroform-$d_3$, internal standard: tetramethylsilane): d (ppm) 2.46 (s, 3H), 4.81 (t, 2H), 7.18-7.72 (m, 19H)

[Reaction Scheme 13]

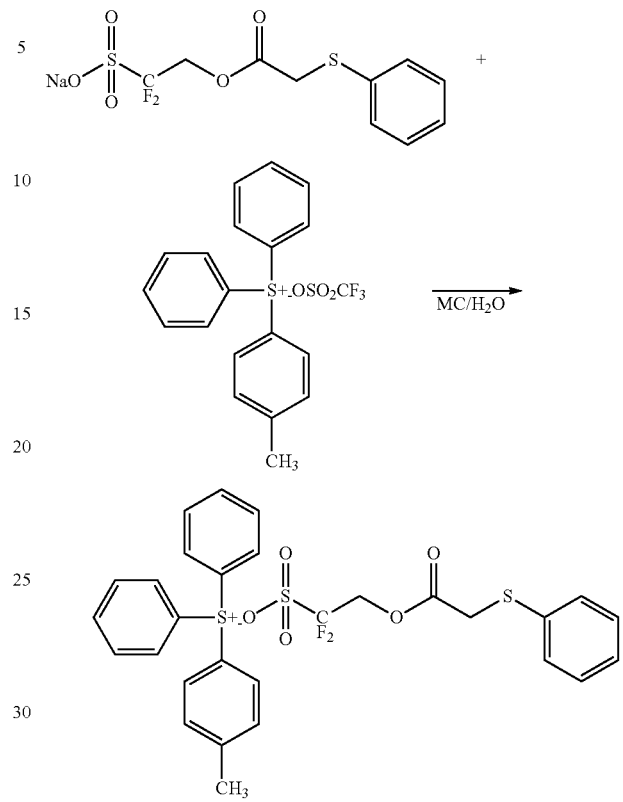

Synthesis Example 7

Figure 13:
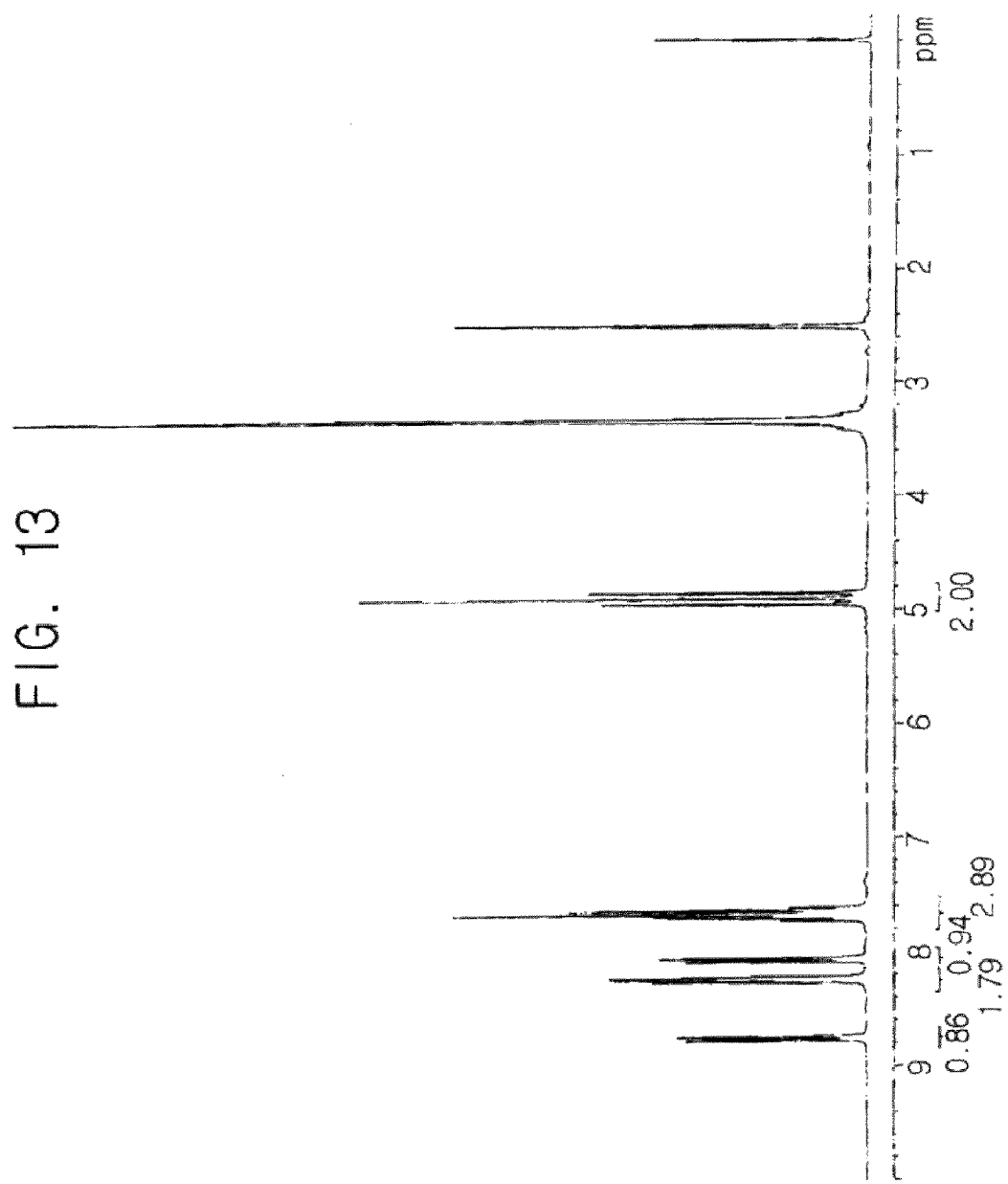
FIG. 13 is a $^1$H-NMR spectrum of a compound produced according to another embodiment of the present invention.

<1> The reaction described in <2> of Synthesis Example 1 was performed under the same conditions, except that 1-naphthoyl chloride (12.2 ml) was used instead of benzoyl chloride as the reactant to react with alcohol, and thus 17 g (yield 93%) of 1-naphthoyloxymethyl difluoromethanesulfonic acid sodium salt as shown in the following reaction scheme 14 was obtained. The structure of the product was confirmed by $^1$H-NMR (see FIG. 13).

$^1$H-NMR (dimethylsulfoxide-$d_6$, internal standard: tetramethylsilane): d (ppm) 4.91 (t, 2H), 7.65 (m, 3H), 8.13 (d, 1H), 8.24 (m, 2H), 8.78 (d, 1H)

[Reaction Scheme 14]

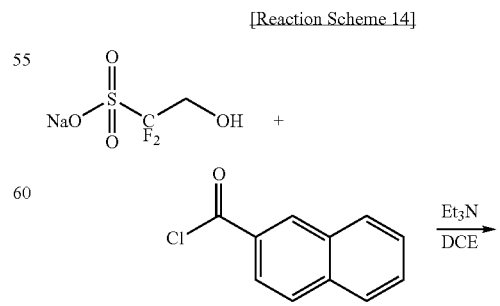

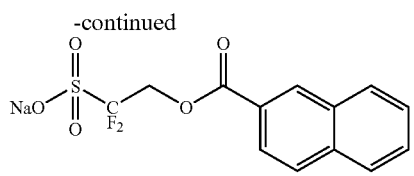

Figure 14:
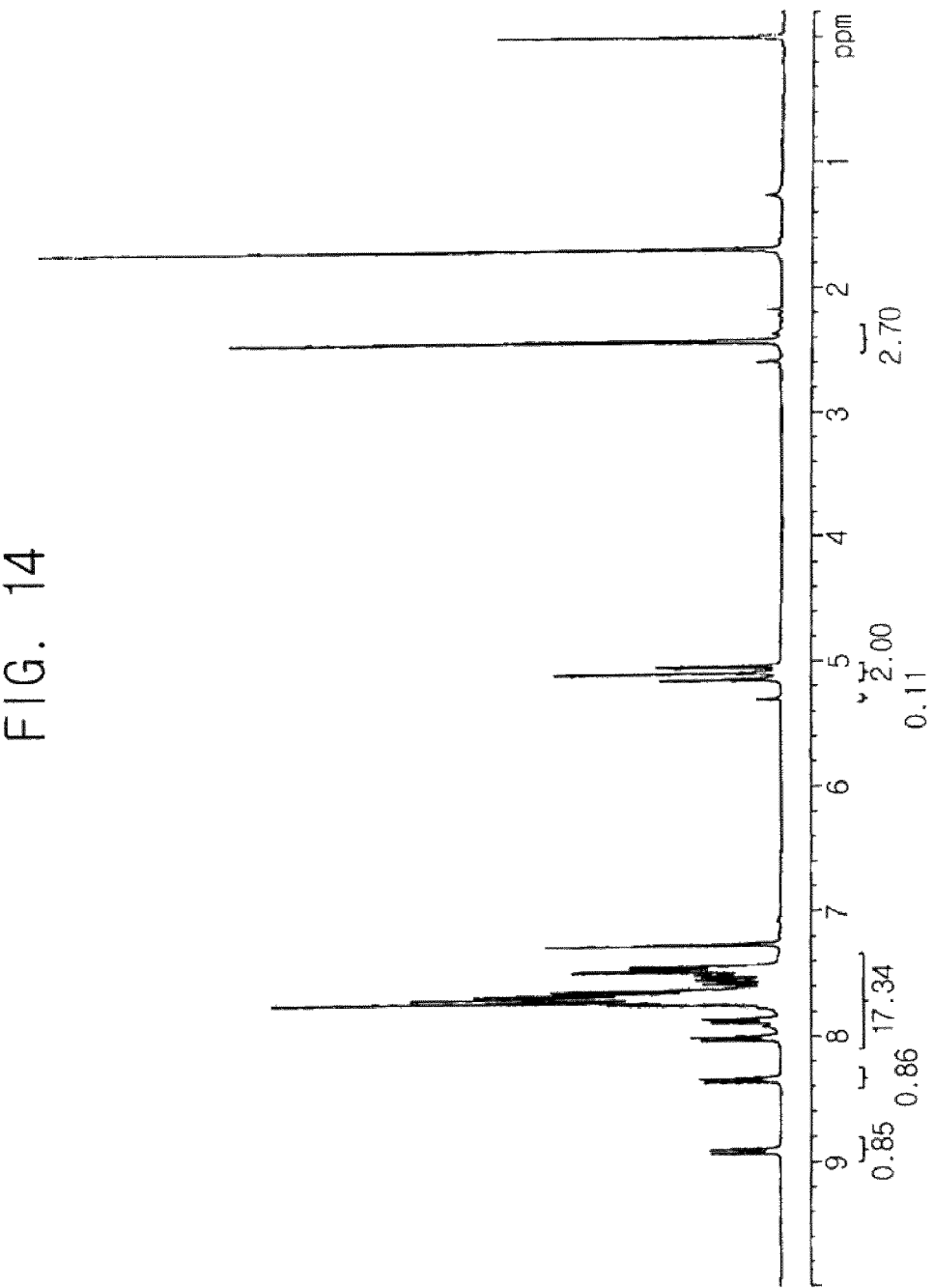
FIG. 14 is a $^1$H-NMR spectrum of a compound produced according to another embodiment of the present invention.

<2> The reaction described in <3> of Synthesis Example 1 was performed under the same conditions, except that the 1-naphthoyloxymethyl difluoromethanesulfonic acid sodium salt (2.61 g) produced in <1> of Synthesis Example 7 above was used instead of the benzoyloxymethyldifluorosulfonic acid sodium salt in the reaction with diphenylmethylphenylsulfonium trifluoromethanesulfonate salt, and thus 3.92 g (yield 94.45%) of 1-naphthoic acid 2,2-difluoro-2-sulfoethyl ester diphenylmethylphenylsulfonium salt as shown in the following reaction scheme 15 was obtained. The structure of the product was confirmed by $^1$H-NMR (see FIG. 14).

$^1$H-NMR (chloroform-$d_3$, internal standard: tetramethylsilane): d (ppm) 2.43 (s, 3H), 5.09 (t, 3H), 7.44-7.72 (m, 17H), 7.86 (d, 1H), 8.01 (d, 1H), 8.34 (d, 1H), 8.90 (d, 1H)

[Reaction Scheme 15]

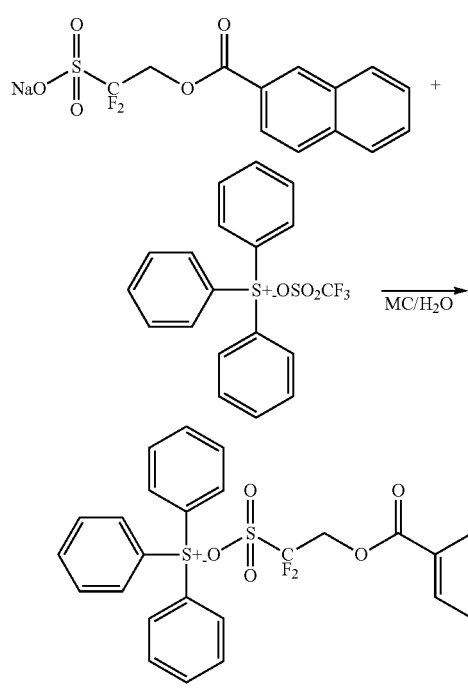

Synthesis Example 8

Figure 15:
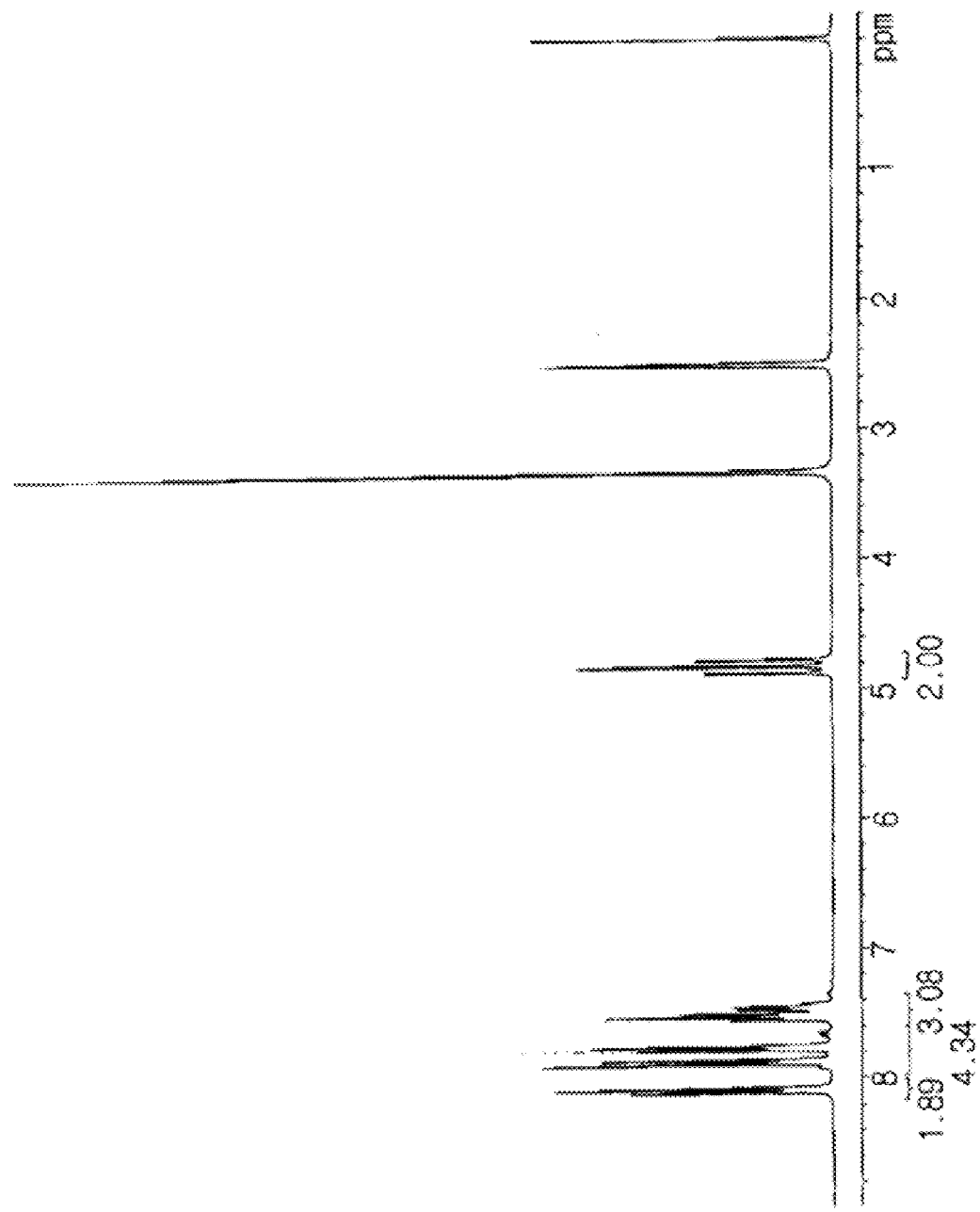
FIG. 15 is a $^1$H-NMR spectrum of a compound produced according to another embodiment of the present invention.

<1> The reaction described in <2> of Synthesis Example 1 was performed under the same conditions, except that 4-phenylbenzoyl chloride (17.7 ml) was used instead of benzoyl chloride as the reactant to react with alcohol, and thus 16 g (yield 95.8%) of 4-phenylbenzoyloxymethyl difluoromethanesulfonic acid sodium salt as shown in the following reaction scheme 16 was obtained. The structure of the product was confirmed by $^1$H-NMR (see FIG. 15).

$^1$H-NMR (dimethylsulfoxide-$d_6$, internal standard: tetramethylsilane): d (ppm) 4.82 (t, 3H), 7.45-8.17 (m, 9H)

[Reaction Scheme 16]

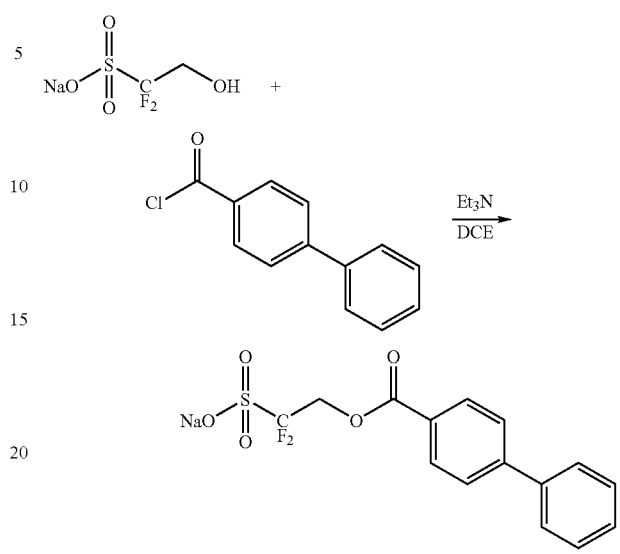

Figure 16:
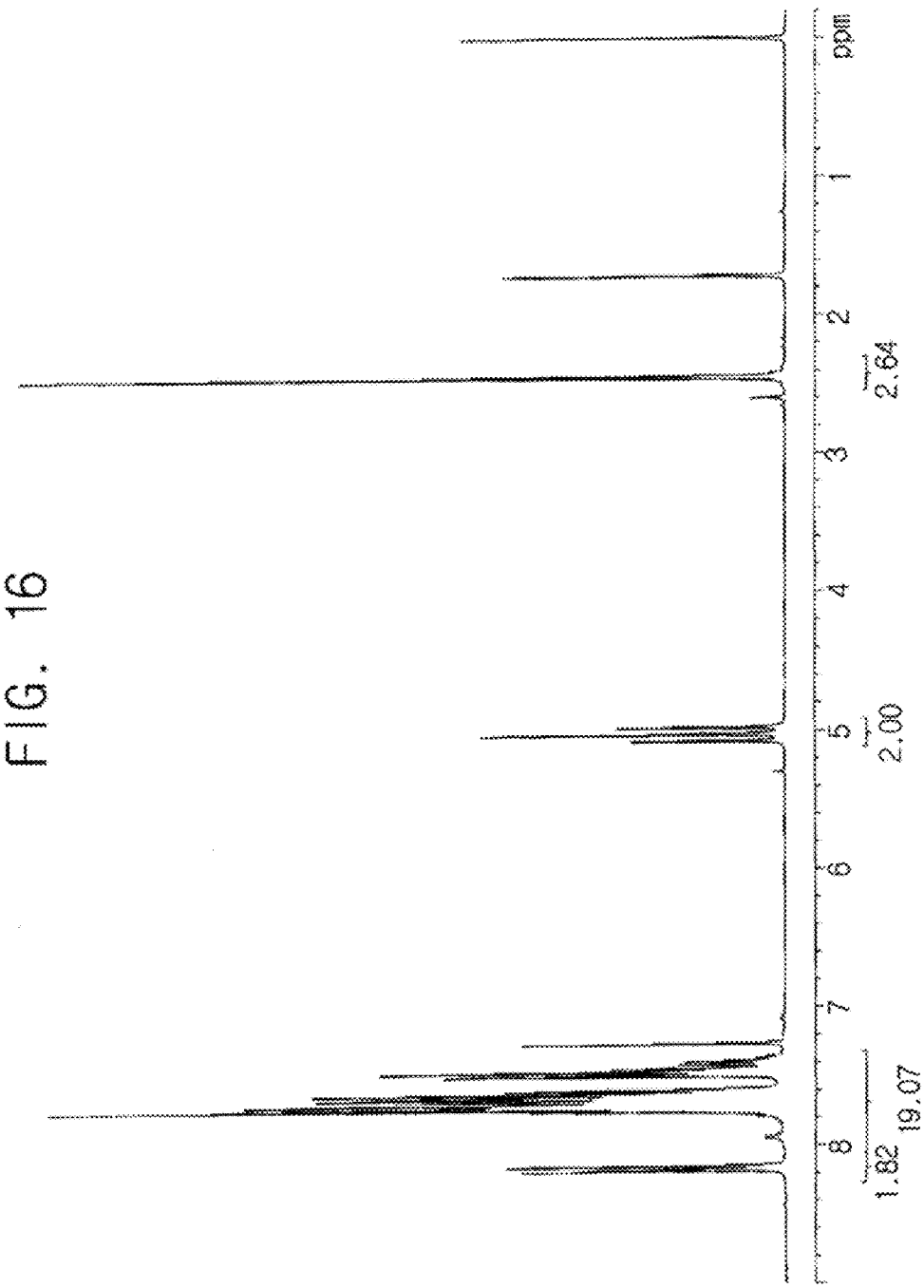
FIG. 16 is a $^1$H-NMR spectrum of a compound produced according to another embodiment of the present invention.

<2> The reaction described in <3> of Synthesis Example 1 was performed under the same conditions, except that the 4-phenylbenzoyloxymethyl difluoromethanesulfonic acid sodium salt (2.81 g) produced in <1> of Synthesis Example 8 above was used instead of the benzoyloxymethyldifluorosulfonic acid sodium salt in the reaction with diphenylmethylphenylsulfonium trifluoromethanesulfonic acid sodium salt, and thus 3.71 g (yield 85.7%) of 4-phenylbenzoic acid 2,2-difluoro-2-sulfoethyl ester diphenylmethylphenylsulfonium salt as shown in the following reaction scheme 17 was obtained. The structure of the product was confirmed by $^1$H-NMR (see FIG. 16).

$^1$H-NMR (chloroform-$d_3$, internal standard: tetramethylsilane): d (ppm) 2.44 (s, 3H), 5.02 (t, 2H), 7.44-7.74 (m, 21H), 8.15 (d, 2H)

[Reaction Scheme 17]

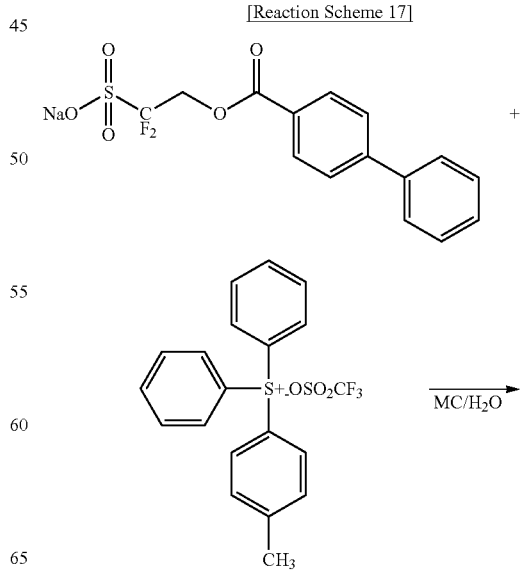

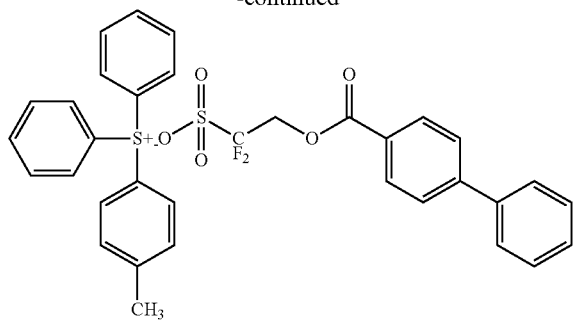

Synthesis Example 9

<1> The reaction described in <2> of Synthesis Example 1 was performed under the same conditions, except that 9-anthracenecarbonyl chloride (19.6 g) was used instead of benzoyl chloride as the reactant to react with alcohol, and thus 21 g (yield 99%) of 9-anthracenecarbonyloxymethyl difluoromethanesulfonic acid sodium salt as shown in the following reaction scheme 18 was obtained. The structure of the product was confirmed by $^1$H-NMR.

$^1$H-NMR (dimethylsulfoxide-$d_6$, internal standard: tetramethylsilane): d (ppm) 5.18 (t, 2H), 7.62 (m, 4H), 8.14 (dd, 4H), 8.84 (s, 1H)

[Reaction Scheme 18]

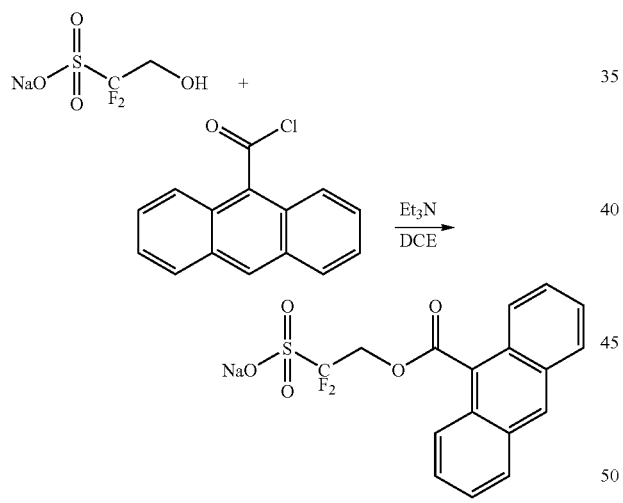

<2> The reaction described in <3> of Synthesis Example 1 was performed under the same conditions, except that the 9-anthracenecarbonyloxymethyl difluoromethanesulfonic acid sodium salt (3.82 g) produced in <1> of Synthesis Example 9 above was used instead of the benzoyloxymethyldifluorosulfonic acid sodium salt in the reaction with diphenylmethylphenylsulfonium trifluoromethanesulfonic acid sodium salt, and thus 3.86 g (yield 85.6%) of 9-anthracenecarboxylic acid 2,2-difluoro-2-sulfoethyl ester diphenylmethylphenylsulfonium salt as shown in the following reaction scheme 19 was obtained. The structure of the product was confirmed by $^1$H-NMR.

$^1$H-NMR (chloroform-$d_3$, internal standard: tetramethylsilane): d (ppm) 2.41 (s, 3H), 5.32 (t, 2H), 7.41-8.11 (m, 22H), 8.51 (s, 1H)

[Reaction Scheme 19]

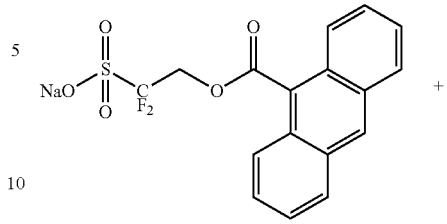

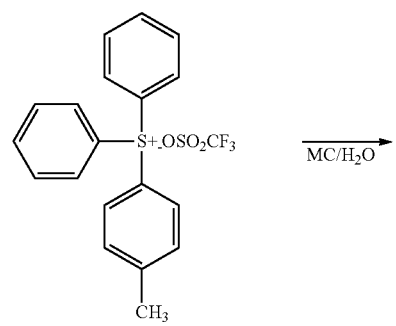

Synthesis Example 10

<1> 7 g of the benzoic acid 2,2-difluoro-2-sulfoethyl ester sodium salt produced in <2> of Synthesis Example 1, and 7 g of diphenyl-t-butoxycarbonylmethoxyphenylsulfonium trifluoromethanesulfonate salt were dissolved in 70 ml of dichloromethane and 70 ml of water, and the mixture was stirred vigorously for 3 hours to perform a two-layer reaction.

After completion of the stirring, a small portion of the organic layer was removed, and the progress of the reaction was confirmed by $^{19}$F-NMR. When the reaction was completed, the organic layer was collected, and the solvent was removed. The residue was washed using dichloromethane, which is a good solvent, and hexane, which is a poor solvent. The solvent was removed, and the residue was dried under reduced pressure to obtain 8.5 g (yield 94%) of benzoic acid 2,2-difluoro-2-sulfoethyl ester diphenyl-t-butoxycarbonylmethoxyphenylsulfonium salt. The structure of the product was confirmed by $^1$H-NMR.

$^1$H-NMR (chloroform-$d_3$, internal standard: tetramethylsilane): d (ppm) 1.48 (s, 9H), 4.62 (s, 2H), 4.76 (t, 2H), 7.17-7.77 (m, 17H), 8.11 (d, 2H)

[Reaction Scheme 20]

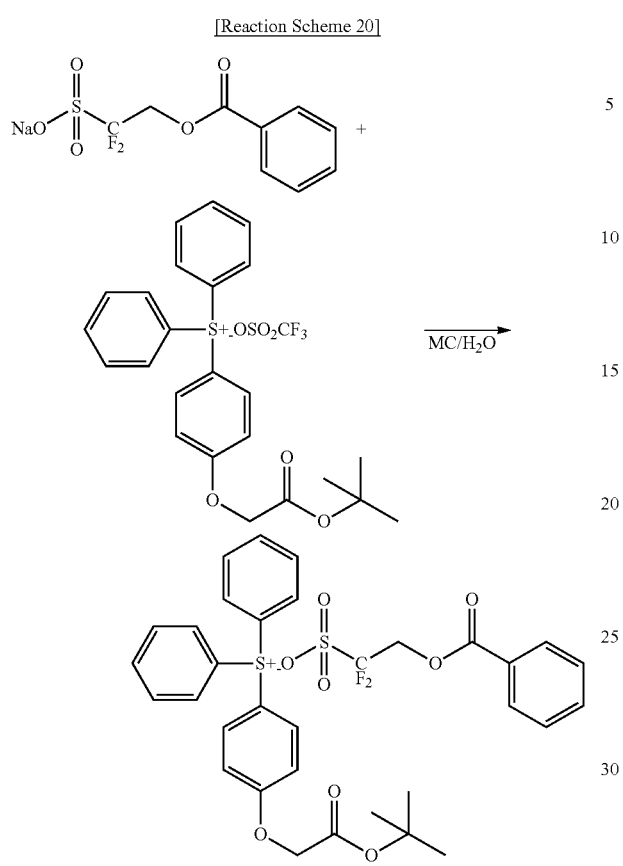

Synthesis Example 11

<1> 8.9 g of the benzoic acid 2,2-difluoro-2-sulfoethyl ester sodium salt produced in <2> of Synthesis Example 1, and 7 g of diphenylfluorophenylsulfonium trifluoromethanesulfonic acid sodium salt were dissolved in 70 ml of dichloromethane and 70 ml of water, and the mixture was stirred vigorously for 3 hours to perform a two-layer reaction.

After completion of the stirring, a small portion of the organic layer was removed, and the progress of the reaction was confirmed by $^{19}$F-NMR. When the reaction was completed, the organic-layer was collected, and the solvent was removed. The residue was washed using dichloromethane, which is a good solvent, and hexane, which is a poor solvent. The solvent was removed, and the residue was dried under reduced pressure to obtain 8.4 g (yield 92.5%) of benzoic acid 2,2-difluoro-2-sulfoethyl ester diphenylfluorophenylsulfonium salt. The structure of the product was confirmed by $^{1}$H-NMR.

$^{1}$H-NMR (chloroform-$d_3$, internal standard: tetramethylsilane): d (ppm) 4.82 (t, 2H), 7.17-7.77 (m, 17H), 8.09 (d, 2H)

[Reaction Scheme 21]

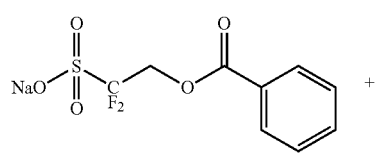

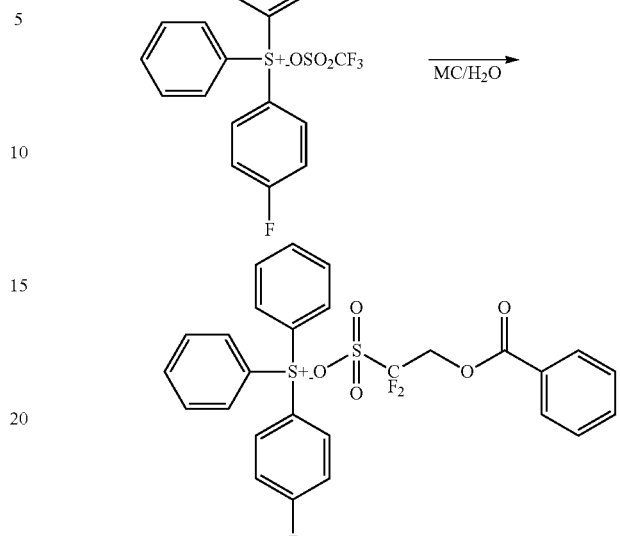

Resin Synthesis Example 1

3-Bicyclo[2.2.1]hept-5-en-2-yl-3-hydroxypropionic acid t-butyl ester (hereinafter, abbreviated as BHP), 1-methyladamantane acrylate and γ-butyrolactone methylacrylate were added in a reaction vessel at a molar ratio of 1:1:1 (33 parts:33 parts:33 parts), and as a polymerization solvent, 1,4-dioxane was used in an amount of three-fold the total mass of the reaction monomers, while azobisisobutyronitrile was used as an initiator in a proportion of 4 mol % based on the total molar amount of the monomers. The resulting mixture was allowed to react for 16 hours at 65° C. After completion of the reaction, n-hexane was added to the reaction solution to obtain a precipitate, and the precipitate was dried in a vacuum to obtain a resin having the following structure. As a result, a copolymer having a weight average molecular weight of about 8,500 was obtained.

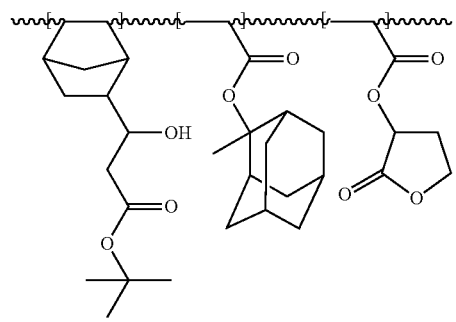

Preparation of Resist, Examples 1 to 3 and Comparative Example 1

Example 1

Preparation of Resist 100 parts by weight of the resin obtained in Resin Synthesis Example 1, 4 parts by weight of adamantane-1-carboxylic acid 2,2-difluoro-2-sulfoethyl ester diphenylmethylphenylsulfonium salt produced in Synthesis Example 1 as an acid generator, and 0.5 parts by weight of tetramethylammonium hydroxide as a basic additive were dissolved in 1,000 parts by weight of propylene glycol methyl ether acetate, and the solution was filtered through a membrane filter having a pore size of 0.2 μm, to prepare a resist.

The obtained resist solution was applied on a substrate using a spinner, and dried at 110° C. for 90 seconds to form a film having a thickness of 0.20 μm. The formed film was exposed using an ArF excimer laser stepper (numerical aperture of lens: 0.78), and then the exposed film was thermally treated at 110° C. for 90 seconds. Subsequently, the film was developed for 40 seconds using a 2.38 wt % aqueous solution of tetramethylammonium hydroxide, and was washed and dried to form a resist pattern.

The developability with the aqueous solution of tetramethylammonium hydroxide, and the adhesiveness of the formed resist pattern to a substrate were both good. The resolution was 0.07 μm, and the sensitivity was 12 mJ/cm$^2$.

Among the results of the current Example, in regard to the line edge roughness (LER), the roughness of pattern was observed for a 0.10-μm line-and-space (L/S) pattern formed after development, and the extent of improvement in terms of LER was graded from 1 to 5, while the pattern obtained from a Comparative Example was graded 1 (a larger number indicates better LER).

In regard to the sensitivity, the amount of exposure which results in the formation of a 0.10-μm line-and-space (L/S) pattern with a line width of 1:1 after development, was designated as the optimum amount of exposure, and this optimum amount of exposure was considered as the sensitivity. The minimum pattern dimension resolved at this sensitivity was designated as the resolution.

Examples 1 to 3

The photoacid generators (PAG) obtained in Synthesis Example 1-<3>, Synthesis Example 2-<2> and Synthesis Example 3-<2> were respectively used together with the resin produced in the Resin Synthesis Example 1 above and a basic additive. Each of the mixtures was dissolved in 1,000 parts by weight of propylene glycol methyl ether acetate, and then the solution was filtered through a membrane filter having a pore size of 0.2 μm. Thus, the resist compositions indicated in the following Table 1 (the parts are on the weight basis) were obtained. Positive resist patterns were formed in the same manner as in Example 1, and various evaluations were performed for the resulting resist patterns. The evaluation results are presented in Table 1 below.

Synthesis Example 3

Comparative Example 1

Triphenylsulfonium Triflate

[Evaluation Results]

The substances of the present invention produced by introducing an aromatic ring to the anion of photoacid generators had lower diffusion rates of acid and shorter distances of diffusion as compared to conventional photoacid generators such as triflates and nonaflates, while maintaining similar acidities to the acidity of triflates. Thus, the substances were found to have appropriate characteristics for the realization of finer L/S patterns. The substances also exhibited much better performance from the aspects of LER and resolution than the conventional triflate type agents, as can be seen from the table above. The introduction of aromatic rings to the anion did not cause any particularly problem in the transparency upon irradiation with light. The photoacid generators of the present invention has advantages that once acid is generated and converted to an anion form, the aromatic ring does not exert any influence on the transparency, and that the diffusion rate and the distance of diffusion of acid can be controlled by the size of the aromatic ring, thus showing features that make the photoacid generators of the present invention distinctive from conventional photoacid generators.

The acid generator according to the present invention has an advantage of having a characteristic that the diffusion rate of acid, the distance of diffusion, the acidity, and the transmissibility at the time of using an ArF light source can be appropriately controlled by introducing an anion group containing an aromatic ring.

What is claimed is:

1. An acid generator represented by the following formula (1):

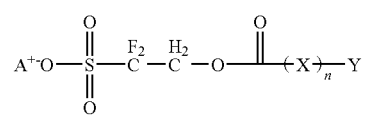

[Formula 1]

wherein X represents an alkylene group having 1 to 10 carbon atoms, —X$_1$—O—X$_2$—, or a heteroatom selected from the group consisting of nitrogen (N), sulfur (S) and fluorine (F); X$_1$ and X$_2$ each independently represent an alkylene group having 1 to 10 carbon atoms; Y represents a cyclic hydrocar-

TABLE 1

|  | Resin (100 parts by weight) | *PAG (parts by weight) | *Base (parts by weight) | Sensitivity (mJ/cm$^2$) | Resolution (nm) | LER |
|---|---|---|---|---|---|---|
| Example 1 | Resin Syn. Ex. 1 | 4.0 | 0.5 | 12 | 70 | 5 |
| Example 2 | Resin Syn. Ex. 1 | 4.0 | 0.5 | 12 | 80 | 3 |
| Example 3 | Resin Syn. Ex. 1 | 4.0 | 0.5 | 12 | 70 | 3 |
| Comp. Ex. 1 | Resin Syn. Ex. 1 | 4.0 | 0.5 | 14 | 90 | 1 |

*Type of PAG used in Table 1
Example 1: Benzoic acid 2,2-difluoro-2-sulfoethyl ester diphenylfluorophenylsulfonium salt produced in <3> of Synthesis Example 1
Example 2: 3-Fluorobenzoic acid 2,2-difluoro-2-sulfoethyl ester diphenylmethylphenylsulfonium salt produced in <2> of Synthesis Example 2
Example 3: Phenylacetic acid 2,2-difluoro-2-sulfoethyl ester diphenylmethylphenylsulfonium salt produced in <2> of bon group having 5 to 30 carbon atoms and containing one or more aromatic rings, while one or more hydrogen atoms on the ring of the cyclic hydrocarbon group may be substituted by one or more members selected from the group consisting of —O—$Y_1$, —CO—$Y_2$, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group and a cyano group; $Y_1$ and $Y_2$ each independently represent an alkyl group having 1 to 6 carbon atoms; n represents an integer of 0 or 5; and $A^+$ represents an organic counterion.

2. The acid generator according to claim 1, wherein represents a phenyl group, a naphthyl group, an anthryl group, a phenanthrenyl group, a fluorenyl group or a pyrene group, while one or more hydrogen atoms on these rings may be substituted by one or more members selected from the group consisting of —O—$Y_1$, —CO—$Y_2$, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group and a cyano group; and $Y_1$ and $Y_2$ each independently represent an alkyl group having 1 to 6 carbon atoms.

3. The acid generator according to claim 1, wherein Y is selected from the group consisting of groups represented by the following formulas (1-a) to (1-f):

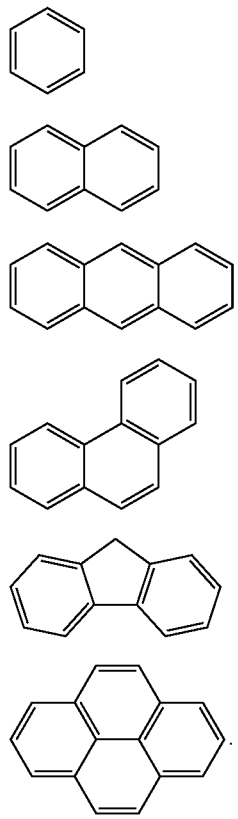

4. The acid generator according to claim 1, wherein the anionic moiety of the formula (1) is selected from the group consisting of groups represented by the following formulas (1-i) to (1-xxxxxi):

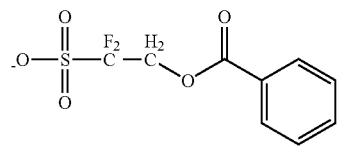

1-i

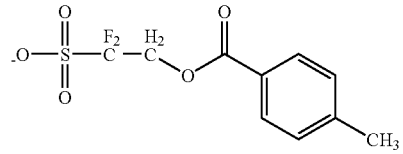

1-ii

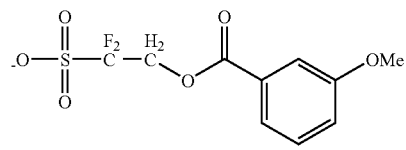

1-iii

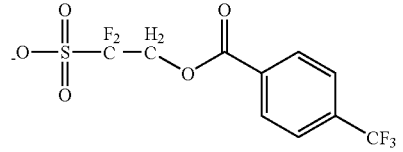

1-iv

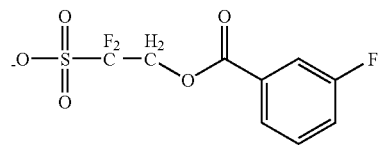

1-v

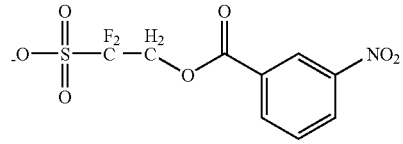

1-vi

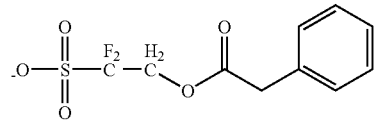

1-vii

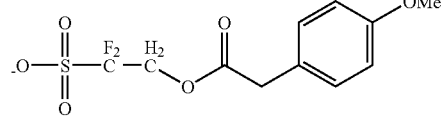

1-viii

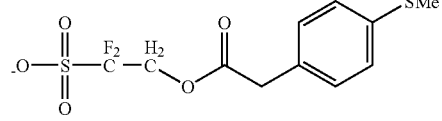

1-ix

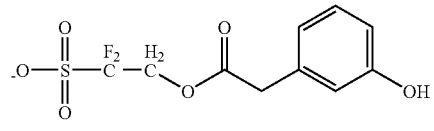

1-x

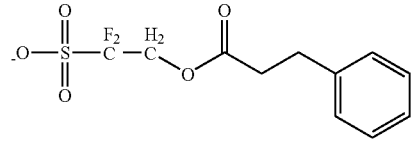

1-xi

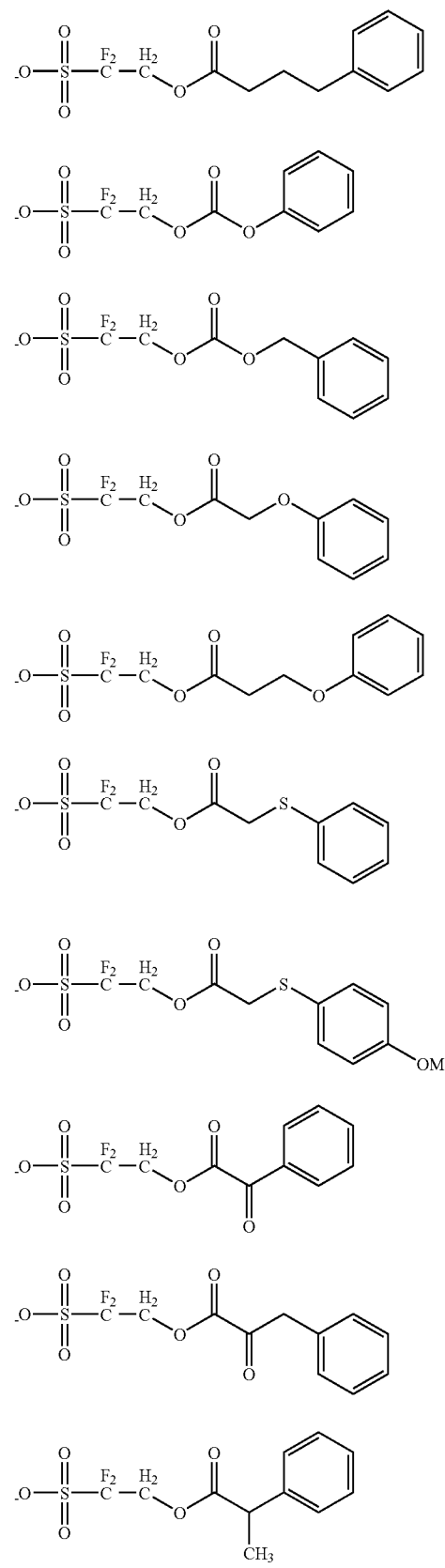
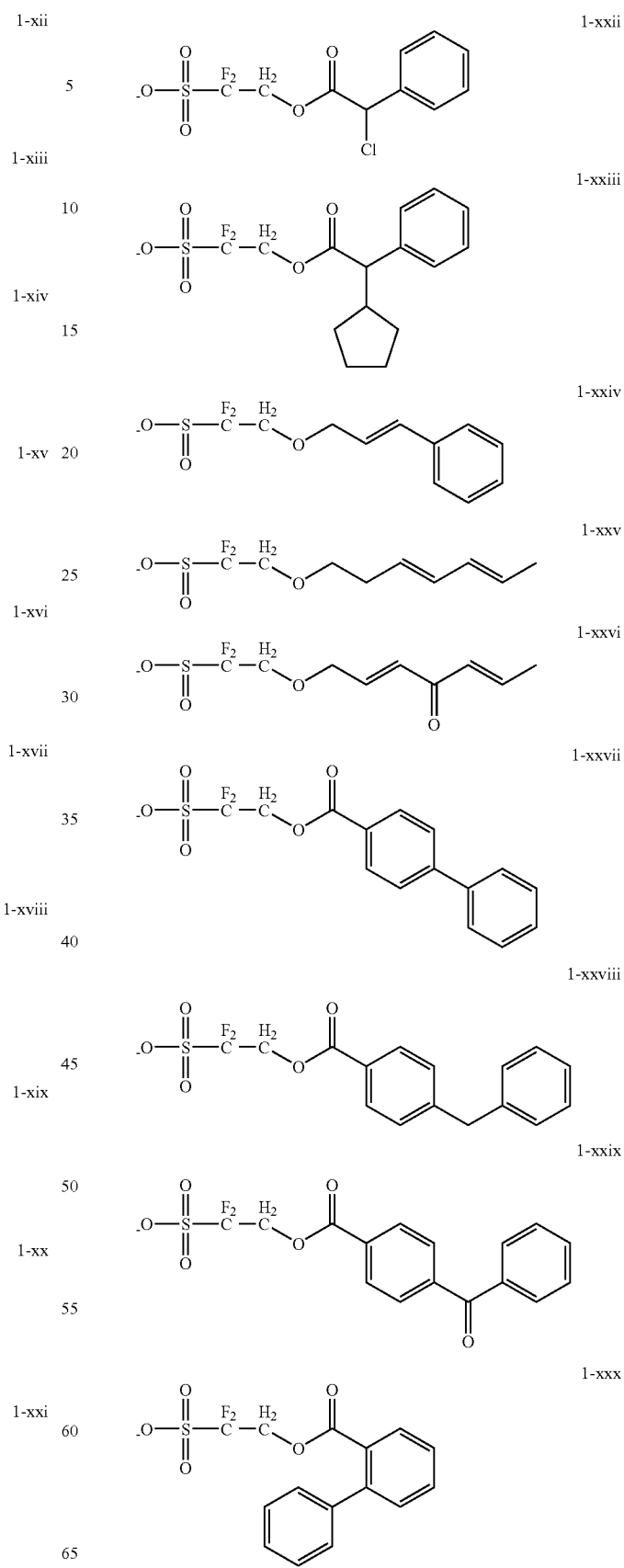

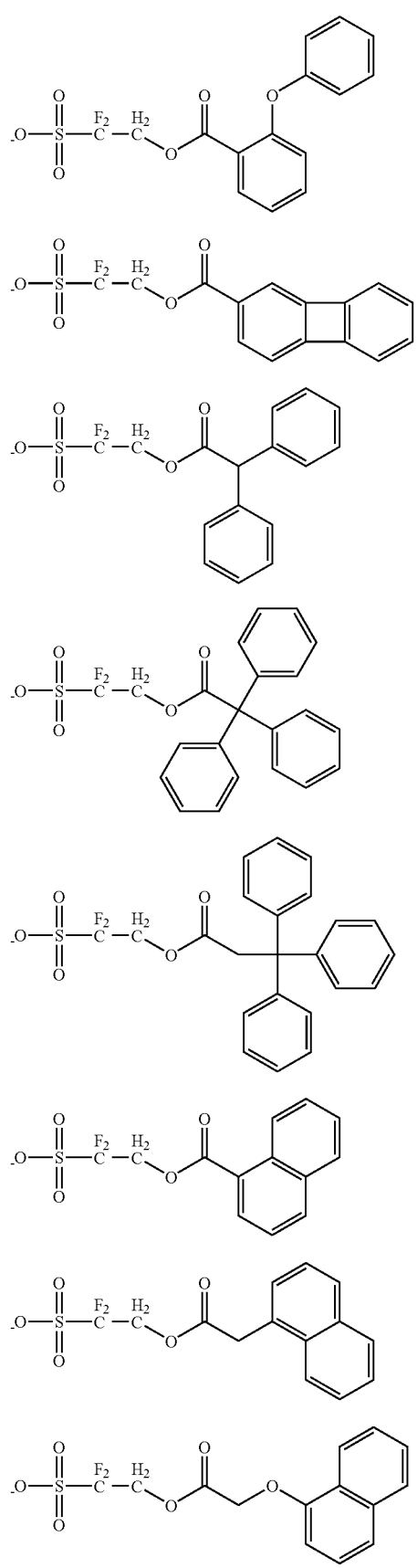
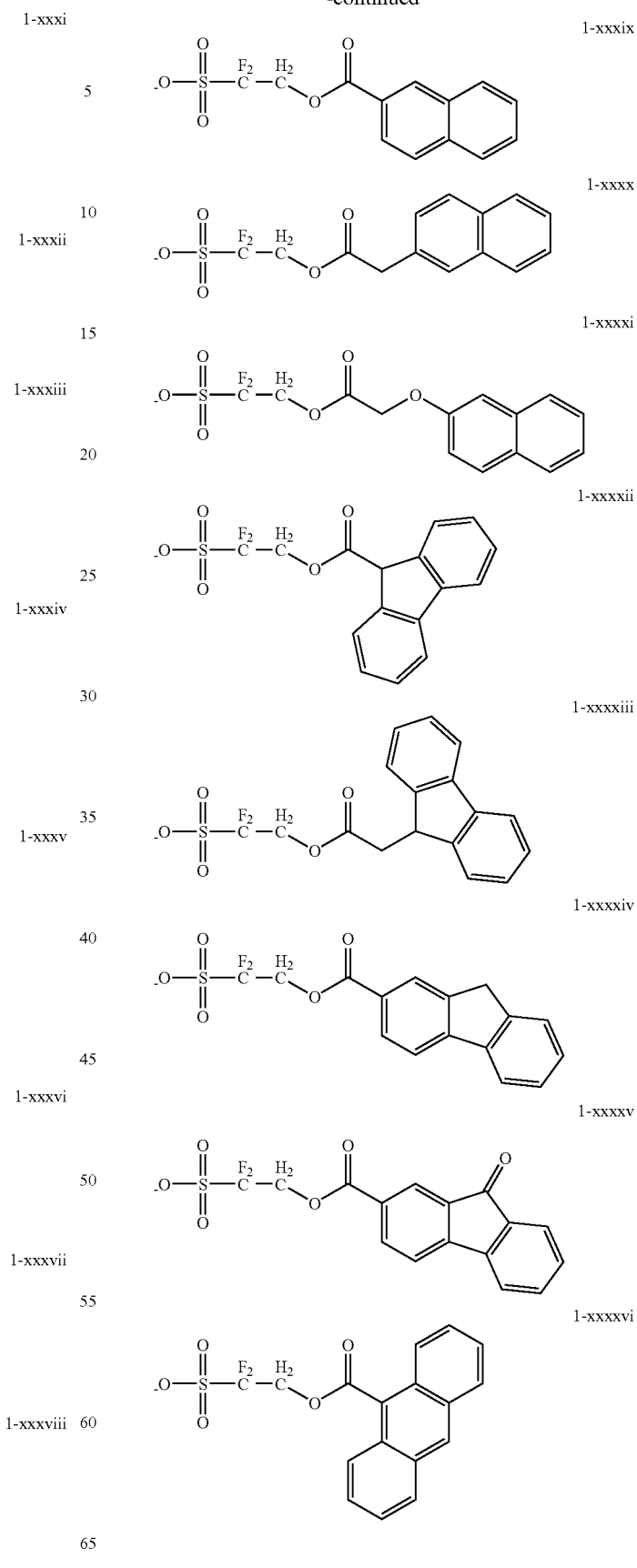

1-xxxxvii

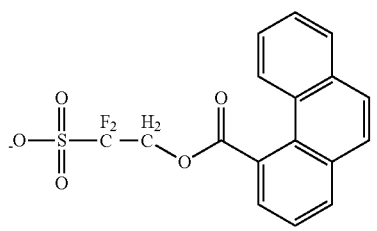

1-xxxxviii

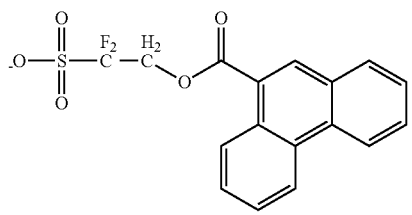

1-xxxxix

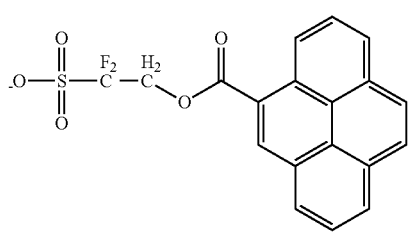

1-xxxxx

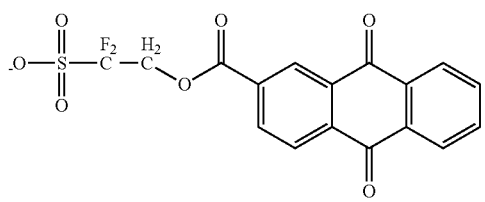

1-xxxxxi

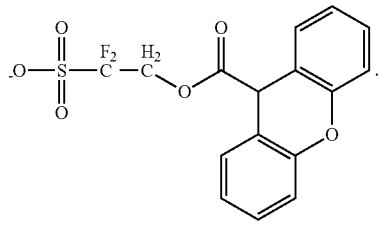

5. The acid generator according to claim 1, wherein the moiety $A^+$ is a cation represented by the following formula (2A) or formula (2B):

[Formula 2A]

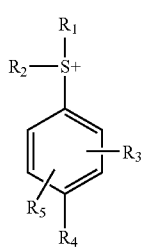

[Formula 2B]

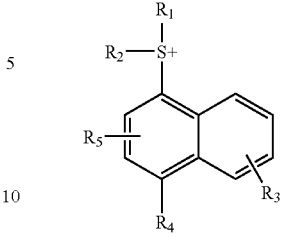

wherein $R_1$ and $R_2$ each independently represent an alkyl group having 1 to 12 carbon atoms, an allyl group having 2 to 12 carbon atoms, a perfluoroalkyl group having 1 to 12 carbon atoms, a benzyl group or an aryl group having 5 to 20 carbon atoms; and $R_3$, $R_4$ and $R_5$ each independently represent a hydrogen atom, an alkyl group having 1 to 12 carbon atoms, a halogen atom, an alkoxy group having 1 to 12 carbon atoms, an aryl group having 5 to 12 carbon atoms, a thiophenoxy group, a thioalkoxy group having 1 to 12 carbon atoms, or an alkoxycarbonylmethoxy group having 1 to 6 carbon atoms.

6. The acid generator according to claim 1, wherein the moiety $A^+$ is a cation represented by the following formula (3A) or formula (3B):

[Formula 3A]

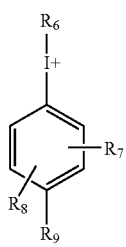

[Formula 3B]

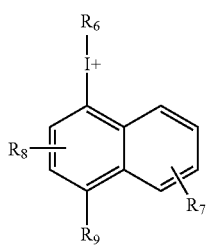

wherein $R_6$ and $R_9$ each independently represent an alkyl group having 1 to 12 carbon atoms, an allyl group having 2 to 12 carbon atoms, a perfluoroalkyl group having 1 to 12 carbon atoms, a benzyl group or an aryl group having 5 to 20 carbon atoms; and $R_7$ and $R_8$ each independently represent a hydrogen atom, an alkyl group having 1 to 12 carbon atoms, a halogen atom, an alkoxy group having 1 to 12 carbon atoms, an aryl group having 5 to 12 carbon atoms, a thiophenoxy group, a thioalkoxy group having 1 to 12 carbon atoms or an alkoxycarbonylmethoxy group having 1 to 6 carbon atoms.

7. The acid generator according to claim 5, wherein the formula (2A) and formula (2B) are selected from the group consisting of the following formulas (2-i) to (2-xx):
2-i
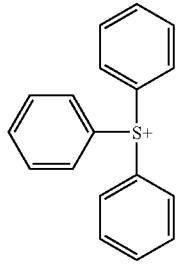
2-ii
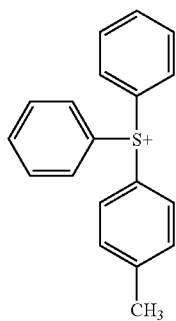
2-iii
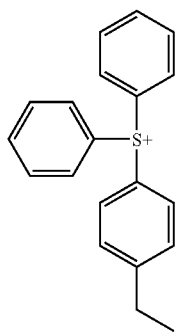
2-iv
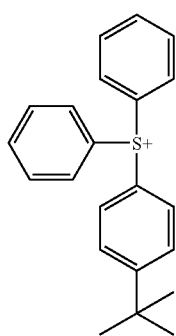
2-v
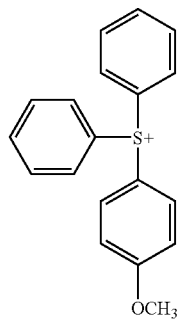
2-vi
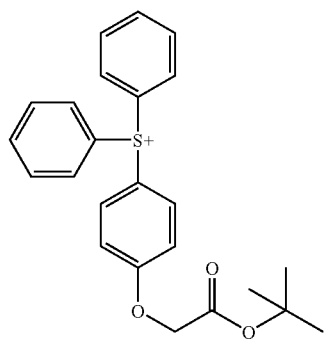
2-vii
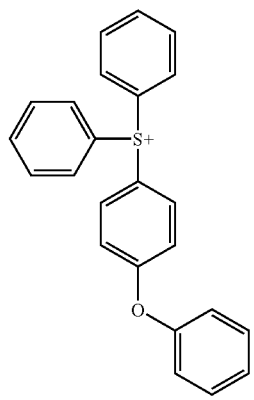
2-viii
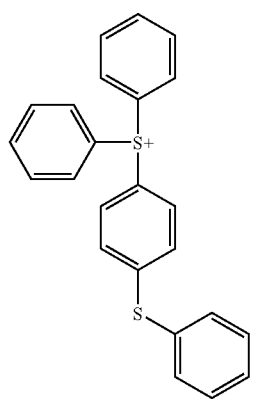

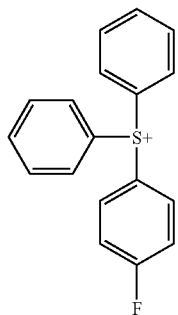
2-ix
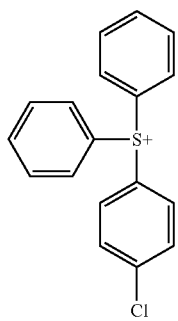
2-x
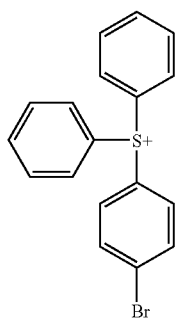
2-xi
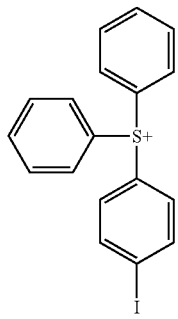
2-xii
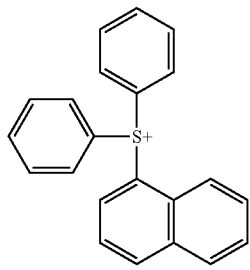
2-xiii
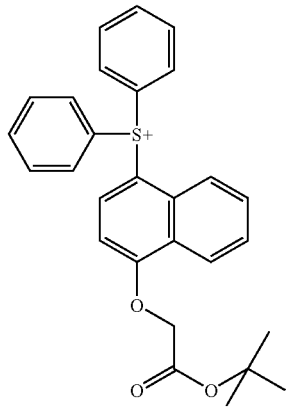
2-xiv
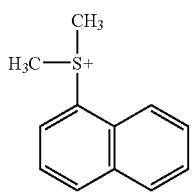
2-xv
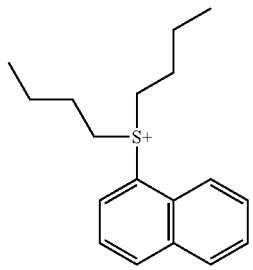
2-xvi
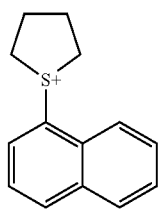
2-xvii
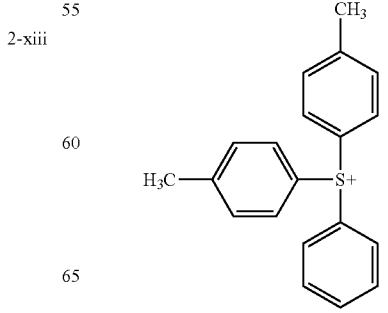
2-xviii

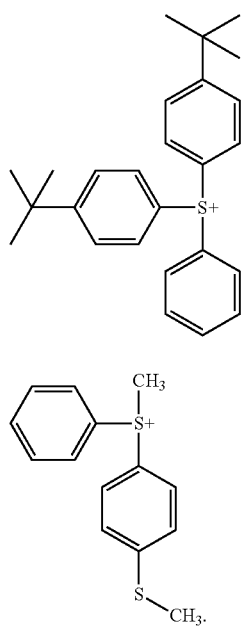

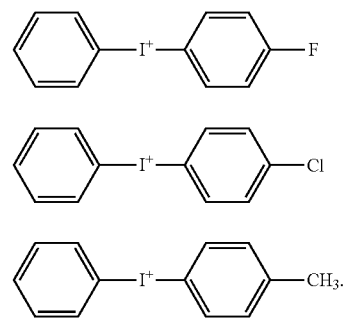

2-xix 3-vii 3-viii 2-xx 3-ix

9. The acid generator according to claim 1, wherein the acid generator is represented by the following formula (4A), formula (4B), formula (4C) or formula (4D):

[Formula 4A]

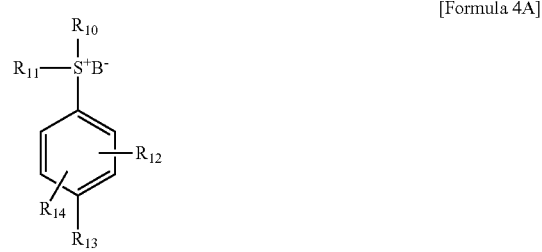

8. The acid generator according to claim 6, wherein the formula (3A) and formula (3B) are selected from the group consisting of the following formulas (3-i) to (3-ix):

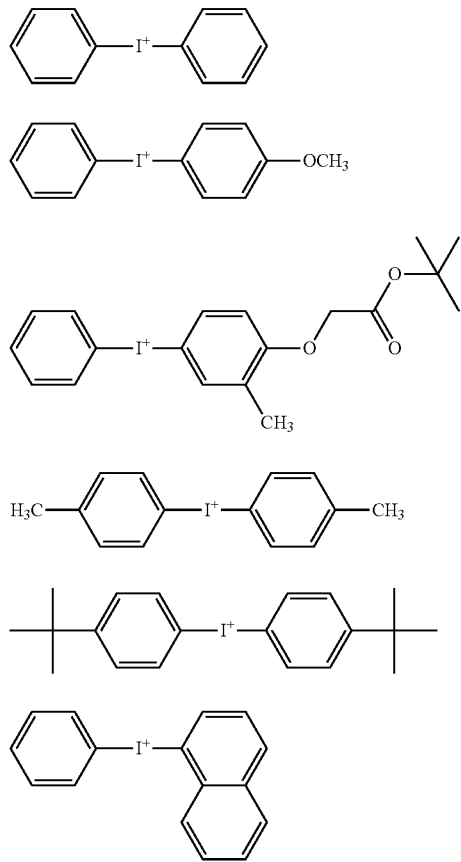

3-i 3-ii

[Formula 4B]

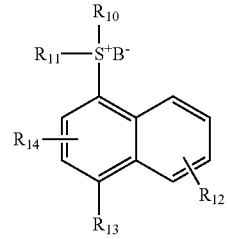

3-iii

[Formula 4C]

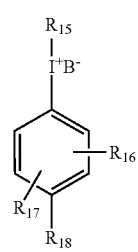

3-iv 3-v

[Formula 4D]

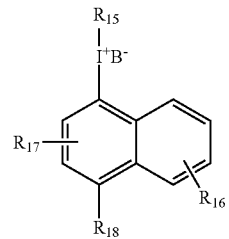

3-vi wherein $R_{10}$, $R_{11}$ and $R_{15}$ each independently represent an alkyl group having 1 to 12 carbon atoms, an allyl group having 2 to 12 carbon atoms, a perfluoroalkyl group having 1 to 12 carbon atoms, a benzyl group or an aryl group having 5 to 20 carbon atoms;

$R_{12}$, $R_{13}$, $R_{14}$, $R_{16}$, $R_{17}$ and $R_{18}$ each independently represent a hydrogen atom, an alkyl group having 1 to 12 carbon atoms, a halogen atom, an alkoxy group having 1 to 12 carbon atoms, an aryl group having 5 to 20 carbon atoms, a thiophenoxy group, a thioalkoxy group having 1 to 12 carbon atoms, or an alkoxycarbonylmethoxy group having 1 to 6 carbon atoms; and B represents any one of the following formula (5) to formula (13):

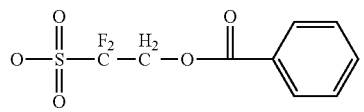

[Formula 5]

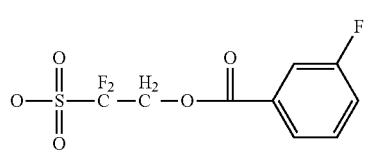

[Formula 6]

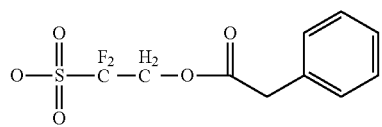

[Formula 7]

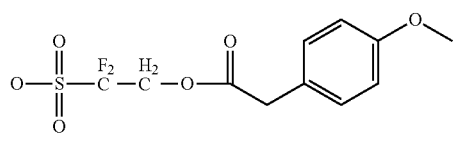

[Formula 8]

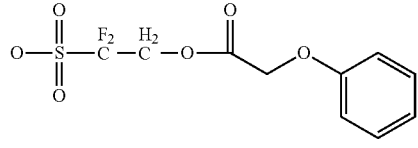

[Formula 9]

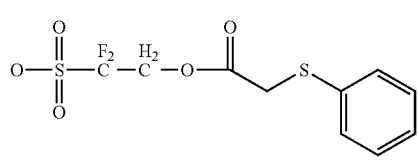

[Formula 10]

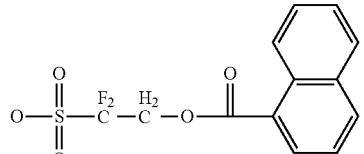

[Formula 11]

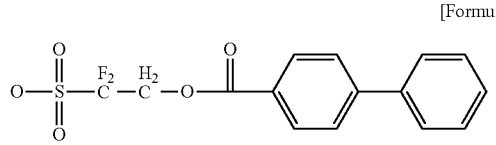

[Formula 12]

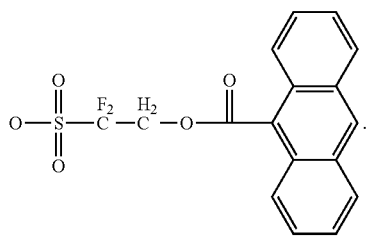

[Formula 13]

10. The acid generator according to claim 1, wherein the compound of formula (1) is produced by a reaction between a salt represented by the following formula (14) and a compound represented by the following formula (15):

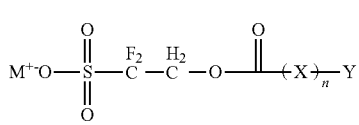

[Formula 14]

wherein X represents an alkyl group having 1 to 10 carbon atoms, $-X_1-O-X_2-$ or a heteroatom selected from the group consisting of N, S and F; $X_1$ and $X_2$ each independently represent an alkylene group having 1 to 10 carbon atoms; Y represents a cyclic hydrocarbon group having 5 to 30 carbon atoms and containing one or more aromatic rings, while one or more hydrogen atoms on the ring of the cyclic hydrocarbon group may be substituted by one or more members selected from the group consisting of $-O-Y_1$, $-CO-Y_2$, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group and a cyano group; $Y_1$ and $Y_2$ each independently represent an alkyl group having 1 to 6 carbon atoms; M represents Li, Na or K; and n represents an integer of 0 or 5;

$A^+Z^-$ [Formula 15]

wherein Z represents $OSO_2CF_3$, $OSO_2C_4F_9$, $OSO_2C_8F_{17}$, $N(CF_3)_2$, $N(C_2F_5)_2$, $N(C_4F_9)_2$, $C(CF_3)_3$, $C(C_2F_5)_3$, $C(C_4F_9)_3$, F, Cl, Br, I, $BF_4$, $ASF_6$ or $PF_6$; and $A^+$ represents an organic counterion.

11. The acid generator according to claim 10, wherein the salt of formula (14) is produced by reacting an alcohol compound represented by the following formula (16) with a carbonyl chloride compound represented by the following formula (17):

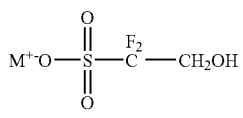

[Formula 16]

wherein M represents Li, Na or K;

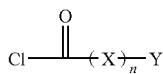

[Formula 17]

wherein X represents a monocyclic or polycyclic hydrocarbon group having 3 to 30 carbon atoms, while at least one or more hydrogen atoms on the monocyclic or polycyclic hydrocarbon group may be substituted by an alkyl or alkoxy group having 1 to 10 carbon atoms, the alkyl or alkoxy group being unsubstituted or substituted with an ether group, an ester group, a carbonyl group, an acetal group, an epoxy group, a nitrile group or an aldehyde group, or by a perfluoroalkyl group having 1 to 4 carbon atoms, a hydroxyalkyl group having 1 to 10 carbon atoms or a cyano group; Y represents a phenyl group, a naphthyl group, an anthryl group, a phenanthrenyl group, a fluorenyl group or a pyrene group, while one or more hydrogen atoms on these rings may be substituted by one or more members selected from the group consisting of —O—$Y_1$, —CO—$Y_2$, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group and a cyano group; and $Y_1$ and $Y_2$ each independently represent an alkyl group having 1 to 6 carbon atoms.

12. The acid generator according to claim 11, wherein the alcohol compound of formula (16) is produced by dissolving an ester compound represented by the following formula (18) in an alcoholic solvent, and then adding a reducing agent dropwise:

[Formula 18]

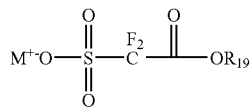

wherein $R_{19}$ represents one selected from the group consisting of hydrogen, methyl, trifluoromethyl, trichloromethyl, tribromomethyl and triiodomethyl; and M represents Li, Na or K.

13. The acid generator according to claim 12, wherein the reducing agent is one or more selected from the group consisting of sodium borohydride, lithium aluminum hydride ($LiAlH_4$), $BH_3$-THF, $NaBH_4$—$AlCl_3$, $NaBH_4$—LiCl and $LiAl(OMe)_3$.

14. A compound represented by the following formula (14):

[Formula 14]

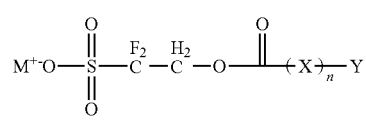

wherein X represents an alkyl group having 1 to 10 carbon atoms, —$X_1$—O—$X_2$— or a heteroatom selected from the group consisting of N, S and F; $X_1$ and $X_2$ each independently represent an alkylene group having 1 to 10 carbon atoms; Y represents a cyclic hydrocarbon group having 5 to 30 carbon atoms and containing one or more aromatic rings, while one or more hydrogen atoms on the ring of the cyclic hydrocarbon group may be substituted by one or more members selected from the group consisting of —O—$Y_1$, —CO—$Y_2$, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group and a cyano group; $Y_1$ and $Y_2$ each independently represent an alkyl group having 1 to 6 carbon atoms; M represents Li, Na or K; and n represents an integer of 0 or 5.

15. A chemically amplified resist composition comprising the acid generator according to claim 1.

\* \* \* \* \*